United States Patent [19]

Nowakowski

[11] Patent Number: 5,409,941
[45] Date of Patent: Apr. 25, 1995

[54] 5-HETEROYL INDOLE DERIVATIVES

[75] Inventor: Jolanta T. Nowakowski, Haddam, Conn.

[73] Assignee: Pfizer Inc., New York, N.Y.

[21] Appl. No.: 94,208

[22] PCT Filed: Feb. 3, 1992

[86] PCT No.: PCT/US92/00556

§ 371 Date: Aug. 6, 1993

§ 102(e) Date: Aug. 6, 1993

[51] Int. Cl.⁶ .............. C07D 417/04; A61K 31/40
[52] U.S. Cl. .................... 514/339; 514/318; 514/323; 514/333; 514/365; 514/374; 546/193; 546/201; 546/256; 546/273; 548/202; 548/203; 548/204; 548/205; 548/235
[58] Field of Search .............. 546/194, 201, 193, 256, 546/273; 548/203, 205, 235, 202, 204; 514/318, 323, 365, 374, 333, 339

[56] References Cited

U.S. PATENT DOCUMENTS 4,833,153  5/1989  Dowle et al. ............. 514/415

FOREIGN PATENT DOCUMENTS 2186874  8/1987  European Pat. Off. ............ 514/374
0303506  2/1989  European Pat. Off. ............ 514/374
0313397  4/1989  European Pat. Off. ............ 514/514
0438230  7/1991  European Pat. Off. ............ 514/374

*Primary Examiner*—C. Warren Ivy
*Assistant Examiner*—Zinna N. Davis
*Attorney, Agent, or Firm*—Peter C. Richardson; Paul H. Ginsburg; Grover F. Fuller, Jr.

[57] ABSTRACT

Compounds of the formula

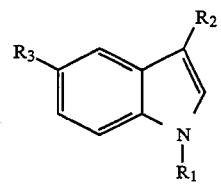

which are useful in treating migraine and other disorders, and intermediates used in the preparation of said compounds.

13 Claims, No Drawings

5-HETEROYL INDOLE DERIVATIVES

This application is a 371 of PCT/US92/00556 filed Feb. 3, 1992.

FIELD OF THE INVENTION

The present invention relates to 5-heteroyl indole derivatives, to processes and intermediates for their preparation, to pharmaceutical compositions containing them and to their medicinal use. The active compounds of the present invention are useful in treating migraine and other disorders.

BACKGROUND OF THE INVENTION

U.S. Pat. No. 4,839,377 and 4,855,314 and European Patent Application Publication Number 313397 refer to 5-substituted 3-aminoalkyl indoles which are said to be useful for the treatment of migraine. British Patent Application 040279 refers to 3-aminoalkyl-1H-indole-5-thioamides and carboxamides which are said to be useful in treating hypertension and Raynaud's disease and also said to be useful in treating migraine.

British Patent Application 2124210A refers to Sumatriptan [3-(2-dimethylamino)ethyl-N-methyl-1H-indole-5-methane sulphonamide] and its analogs which are said to be useful for the treatment of migraine. European Patent Application Publication Number 303506 refers to 3-poly:hydro-pyridyl-5-substituted-1H-indoles. The compounds are said to be 5-$HT_1$-receptor agonists and to have vasoconstrictor activity, as well as to be useful in treating migraine. European Patent Application publication Number 354777 refers to N-piperidinyl:indolyl:ethyl-alkane sulfonamide derivatives. The compounds are said to be useful in treating cephalic pain and are also said to have 5-$HT_1$-receptor agonist and vasoconstrictor activity.

SUMMARY OF THE INVENTION

Compounds of the formula

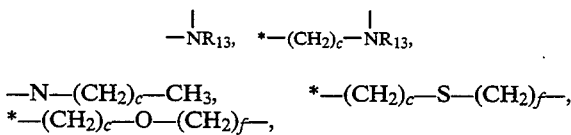

I wherein $R_1$ is hydrogen, $C_1$ to $C_6$ alkyl, phenyl, benzyl, —$COR_4$, or —$SO_2R_4$; $R_2$ is

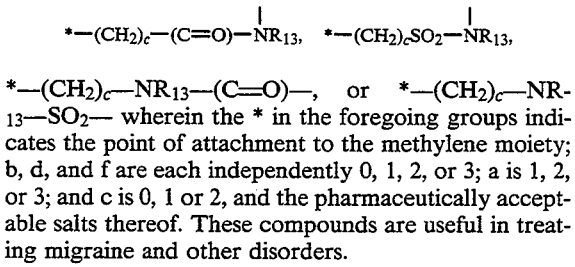

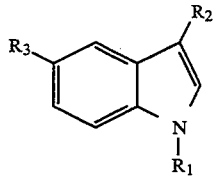

$R_3$ is —$(CH_2)_d$—Z; Z is N 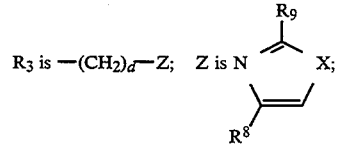 X;

$R_4$ is $C_1$ to $C_6$ alkyl, phenyl, or benzyl; $R_5$ is hydrogen or $C_1$ to $C_6$ alkyl; $R_6$, $R_7$ $R_{11}$, $R_{12}$, and $R_{13}$ are each independently hydrogen or $C_1$ to $C_6$ alkyl; either $R_8$ or $R_9$ is hydrogen, $C_1$ to $C_6$ alkyl, halogen-substituted $C_1$ to $C_6$ alkyl, 1-pyrrolidynylmethyl, 1-piperidynylmethyl, cyclopentylmethyl, cyclohexylmethyl or

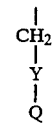

with the other being the bond between $R_3$ and Z; Q is

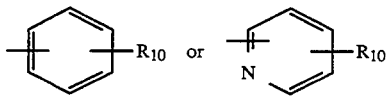

$R_{10}$ is hydrogen, hydroxy, halogen, cyano, nitro, —$CF_3$, —$NR_{11}R_{12}$, $C_1$ to $C_6$ alkyl, or —O—$(CH_2)_b$—$CH_3$; X is S, O, or S→O; Y is a covalent bond, $C_1$ to $C_5$ alkyl, S, O,

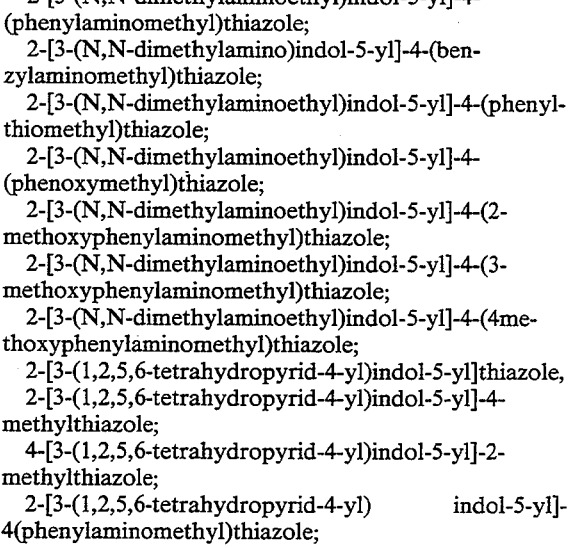

*—$(CH_2)_c$—$NR_{13}$—(C=O)—, or *—$(CH_2)_c$—$NR_{13}$—$SO_2$— wherein the * in the foregoing groups indicates the point of attachment to the methylene moiety; b, d, and f are each independently 0, 1, 2, or 3; a is 1, 2, or 3; and c is 0, 1 or 2, and the pharmaceutically acceptable salts thereof. These compounds are useful in treating migraine and other disorders.

Unless otherwise indicated, the alkyl groups referred to herein, as well as the alkyl moieties of other groups referred to herein (e.g. alkoxy), may be linear or branched, and they may also be cyclic (e.g., cyclopropyl, cyclobutyl, cyclopentyl or cyclohexyl) or be linear or branched and contain cyclic moieties.

The following compounds are particularly preferred:
2-[3-(N,N-dimethylaminoethyl)indol-5-yl]-4-(phenylaminomethyl)thiazole;
2-[3-(N,N-dimethylamino)indol-5-yl]-4-(benzylaminomethyl)thiazole;
2-[3-(N,N-dimethylaminoethyl)indol-5-yl]-4-(phenylthiomethyl)thiazole;
2-[3-(N,N-dimethylaminoethyl)indol-5-yl]-4-(phenoxymethyl)thiazole;
2-[3-(N,N-dimethylaminoethyl)indol-5-yl]-4-(2-methoxyphenylaminomethyl)thiazole;
2-[3-(N,N-dimethylaminoethyl)indol-5-yl]-4-(3-methoxyphenylaminomethyl)thiazole;
2-[3-(N,N-dimethylaminoethyl)indol-5-yl]-4-(4-methoxyphenylaminomethyl)thiazole;
2-[3-(1,2,5,6-tetrahydropyrid-4-yl)indol-5-yl]thiazole,
2-[3-(1,2,5,6-tetrahydropyrid-4-yl)indol-5-yl]-4-methylthiazole;
4-[3-(1,2,5,6-tetrahydropyrid-4-yl)indol-5-yl]-2-methylthiazole;
2-[3-(1,2,5,6-tetrahydropyrid-4-yl) indol-5-yl]-4(phenylaminomethyl)thiazole;

2-[3-(1-methylpiperidin-4-yl)indol-5-yl]-4-(phenylaminomethyl)thiazole;

2-[3-(N,N-dimethylaminoethyl)indol-5-yl]-4-phenylthiazole;

2-[3-(N,N-dimethylaminoethyl)indol-5-yl]-4-benzylthiazole;

2-[3-(N,N-dimethylaminoethyl)indol-5-yl]-4-phenethylthiazole;

2-[3-(Aminoethyl)indol-5-yl]-4-benzylthiazole;

2-[3-(N-Methylaminoethyl)indol-5-yl]-4-benzylthiazole; and

4-[3-(N,N-Dimethylaminoethyl)indol-5-yl]-2-benzylthiazole.

The present invention also relates to a pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound of the formula I or a pharmaceutically acceptable salt thereof effective in treating such condition and a pharmaceutically acceptable carrier.

The present invention also relates to a pharmaceutical composition for treating disorders arising from deficient serotonergic neurotransmission (e.g., depression, anxiety, eating disorders, obesity, drug abuse, cluster headache, migraine, pain, and chronic paroxysmal hemicrania and headache associated with vascular disorders) comprising an amount of a compound of the formula I or a pharmaceutically acceptable salt thereof effective in treating such disorder and a pharmaceutically acceptable carrier.

The present invention also relates to a method for treating a condition selected from hypertension, depression anxiety, eating disorders, obesity, drug abuse, cluster headache, migraine, pain and chronic paroxysmal hemicrania and headache associated with. vascular disorders comprising administering to a mammal (e.g., a human) requiring such treatment an amount of a compound of the formula I or a pharmaceutically acceptable salt thereof effective in treating such disorder.

The present invention also relates to a method for treating disorders arising from deficient serotonergic neurotransmission (e.g., depression, anxiety, eating disorders, obesity, drug abuse, cluster headache, migraine, pain and chronic paroxysmal hemicrania and headache associated with vascular disorders) comprising administering to a mammal (e.g., a human) requiring such treatment an amount of a compound of the formula I or a pharmaceutically acceptable salt thereof effective in treating such disorder.

DETAILED DESCRIPTION OF THE INVENTION

Compounds of the present invention are formed according to the following reaction scheme

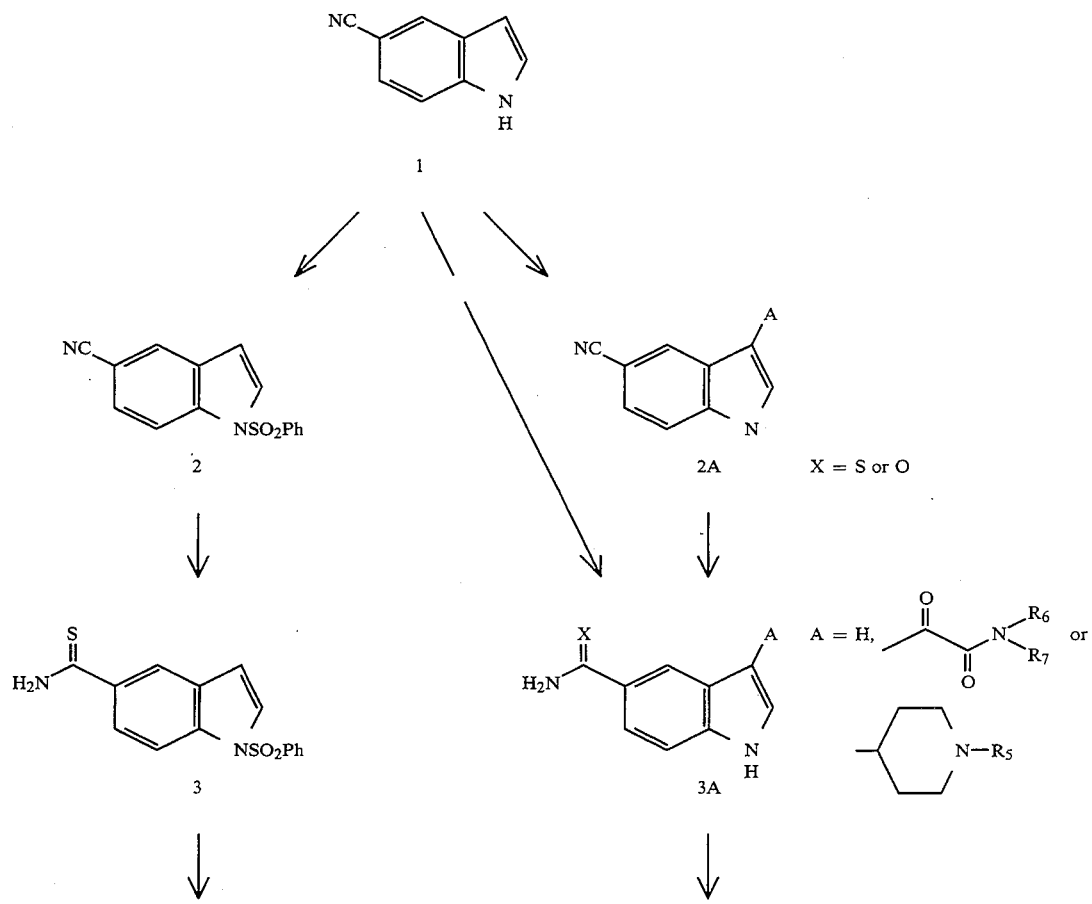

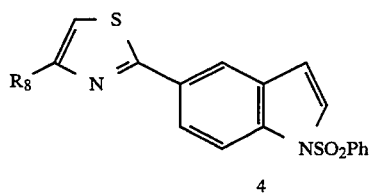

4

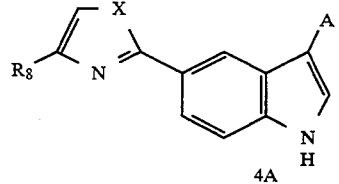

4A where A = H or 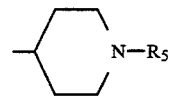   where A = —(CH$_2$)$_2$—N(R$_6$)(R$_7$)

7

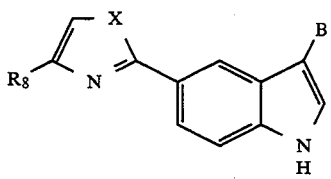

5

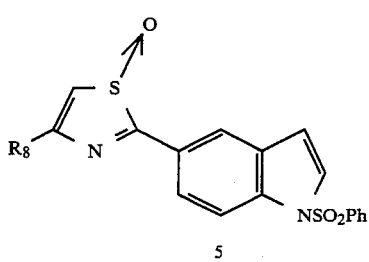

6

B = 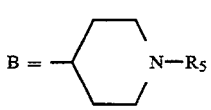

or

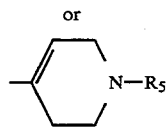

X = S, O, S → O

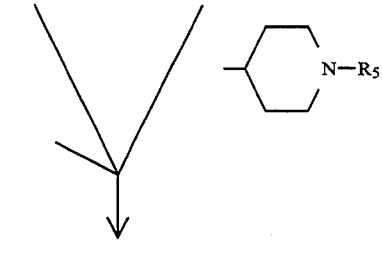

7 where A = —(CH$_2$)$_2$—N(R$_6$)(R$_7$)

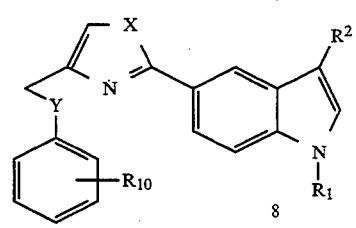

8

R$_2$ = 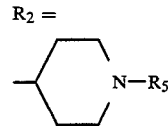

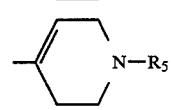

or

—(CH$_2$)$_2$—N(R$_6$)(R$_7$)

The sulfonyl-cyanoindole (2) is formed by reacting the 5-cyanoindole (1) with a base such as sodium hydride, potassium hydride, or n-butyl lithium. The preferred base is sodium hydride. This is followed by the addition of phenylsulfonyl chloride. The reaction is carried out in an inert polar solvent such as diethyl ether, dimethyl formamide or tetrahydrofuran, preferably tetrahydrofuran. The reaction temperature should be from about 0° to ambient temperature (about 25° C.), preferably 0° to 5° C. The sulfonyl moiety acts as a clearable protecting group. Other protecting groups may also be used. Suitable protecting groups include acetyl, p-toluenesulfonyl, and tert-butoxycarbonyl.

The sulfonyl-cyanoindole (2) is converted to the thiocarboxamide (3) by reacting the former with diethyl dithiophosphate under acidic conditions in an inert solvent. The acidic conditions include a range from about pH 1.0 to about pH 5.0 preferably pH 2. Suitable acids for use in the reaction include hydrochloric acid and hydrobromic acid, preferably the former. Suitable solvents include ethyl acetate, diethyl ether, chloroform and methylene chloride, preferably ethyl acetate. The temperature should range from about 20° C. to about 60° C. The preferred temperature is ambient temperature (generally about 25° C.).

The thiazole (4) is formed by reacting the thiocarboxamide (3) with an α-chlorocarbonyl reactant, such as chloroacetaldehyde (forming an unsubstituted ring), chloroacetone (forming a methyl-substituted ring), 1,3- dichloroacetone (forming a chloromethyl-substituted ring), 2-chloroacetophenone (forming a phenyl-substituted ring), or 1-chloro-3-phenyl-2-propanone (forming a benzyl-substituted ring), depending on the desired $R_8$ substituent. This reaction occurs in a polar solvent such as ethanol or tetrahydrofuran, preferably the former. The reaction temperature should be between about 60° C. and about 100° C., preferably the reflux temperature of the solvent.

Thiazole (4) is converted to the corresponding thiazolesulfoxide (5) by reacting the former with an oxidizing agent such as an inorganic peroxide or m-chloroperbenzoic acid, preferably m-chloroperbenzoic acid, in a non-polar solvent. The non-polar solvents useful in the reaction include benzene, hexane, chloroform, or methylene chloride, preferably methylene chloride. The reaction temperature should be between about 0° and about 30° C., preferably ambient temperature.

Alternatively the compounds of interest can be prepared from cyanoindole (1) via the corresponding carboxamide or thiocarboxamide (3A). To form the carboxamide one reacts the cyanoindole (1) with an oxidizing agent under basic conditions in a polar solvent affords carboxamide (3A), where A is hydrogen. The suitable oxidizing agents include inorganic peroxides, preferably hydrogen peroxide. The reaction is carried out in polar solvents such as alcohols, preferably ethanol, at a temperature between about 0° and about 50° C., preferably ambient temperature, at a pH between about 8 and 12, preferably pH 10. The thiocarboxamide (3A) is formed from cyanoindole (1) using the same procedure as described above for converting sulfonylcyanoindole (2) to thiocarboxamide (3).

Alternatively, carboxamide and thiocarboxamide compounds (3A), where A is an amino carbonyl substituent, can be prepared by reacting cyanoindole (1) with a chlorocarbonyl reagent in an inert solvent such as tetrahydrofuran or diethyl ether, preferably aiethyl ether at a temperature of about 0° C. to about 30° C., preferably ambient temperature. The chlorocarbonyl reagent used depends upon the number of desired carbon atoms between the indole and the amine. The chlorocarbonyl reagents include chloroacetyl chloride or oxalyl chloride, preferably the latter, when forming two carbon linkages, and malonyl chloride when forming three carbon linkages. The reaction is then treated with an appropriate primary or secondary amine reagent [HN($R_6R_7$)] to afford indole (2A). In order to form a one carbon linkage between the indole and amine, the indole is converted to the corresponding 3-carboethoxy indole using the chlorocarbonyl reagent ethyl chloroformate and the resulting product is converted to the desired amide, using an appropriate primary or secondary amine reagent [HN($R_6R_7$)]. Carboxamide and thiocarboxamide (3A) are formed from indole (2A) using the same procedures described above for converting cyanoindole (1) to carboxamide (3A) and to thiocarboxamide (3), respectively.

The carboxamide or thiocarboxamide (3A) is converted to the corresponding thiazole or oxazole (4A) using the same procedures as described above for converting thiocarboxamide (3) to thiazole (4).

Thiazoles (4) and (4A), thiazole sulfoxide (5), and oxazole (4A) where A is hydrogen, are transformed into the corresponding nitrogen-containing cyclic compounds (6) in a reaction with the appropriate ketone depending upon the desired side chain, the reaction taking place in the presence of a base. Ketones, such as N-t-butoxy-carbonyl-4-piperidone are utilized when a direct linkage between the indole and nitrogen-containing- cyclic side chain is required. Suitable bases include sodium or potassium alkoxides and alkylmagnesium halides, the preferred base being sodium methoxide. Polar solvents for the reaction include alcohols, dimethylformamide and tetrahydrofuran, with the preferred solvent being methanol. The reaction is conducted at a temperature of between about 60° C. to about 120° C., preferably at about 65° to about 70° C.

Reduction of the amino carbonyl substituent A of thiazole or oxazole (4A) is performed by reduction with a hydride reducing agent in an inert solvent. Suitable hydride reducing agents include lithium aluminum hydride, diborane, and lithium borohydride, preferably diborane. Suitable solvents include ethers, such as diethyl ether, tetrahydrofuran, 1,4-dioxane, 1,2-dimethoxyethane. The preferred solvent is tetrahydrofuran. The reduction is conducted at a temperature of between about 20° and about 100° C., preferably about ambient temperature. The final product is produced by hydrolyzing the reduction product using, for example, water, when lithium aluminum hydride or lithium borohydride are used. Products of the hydride reduction are isolated as a borane complex when diborane is used. The borane complex of the compound 7 on treatment with cesium fluoride in a presence of an inorganic base in a polar solvent is converted into the compound of the formula 7. Suitable inorganic bases include sodium bicarbonate, sodium carbonate and potassium carbonate, preferably sodium carbonate. Polar solvents include alcohols, preferably methanol. The reaction is conducted at a temperature of about 25° C. to about 80° C., preferably at the reflux temperature of the solvent.

As an alternative, when forming compounds having a group at the 3-position, a pyridinyl substituent is added to the cyanoindole (1) prior to introduction of the substituent at the 5-position using the procedure described in the previous paragraph. The pyridinyl group is then reduced, using, for example, palladium hydroxide or palladium on carbon catalyst, preferably the latter to form the corresponding piperidinyl derivative. The reaction is carried out in the presence of hydrogen at a temperature of between about 0° C. and about 50° C., preferably about ambient temperature. A polar solvent should be used such as an alcohol, preferably ethanol.

When a carbon linkage is desired between the thiazole (oxazole or thiazole sulfoxide) and the indole ring, the 5-cyanoindole (1) is converted to a homologous nitrile such as 5-cyanomethylindole utilizing the cyanohydrin method (Chem. Pharm. Bull., 20, 2163 (1972)). The 5-cyanomethylindole is then used to prepare the corresponding thiazole, oxazole or thiazole sulfoxide as described previously (compounds 3, 4 and 5).

In contrast with the 2-indolyl thiazole, oxazole or thiazole sulfoxide compounds described previously, the preparation of the 4-indolyl derivatives is described in the following reaction scheme.

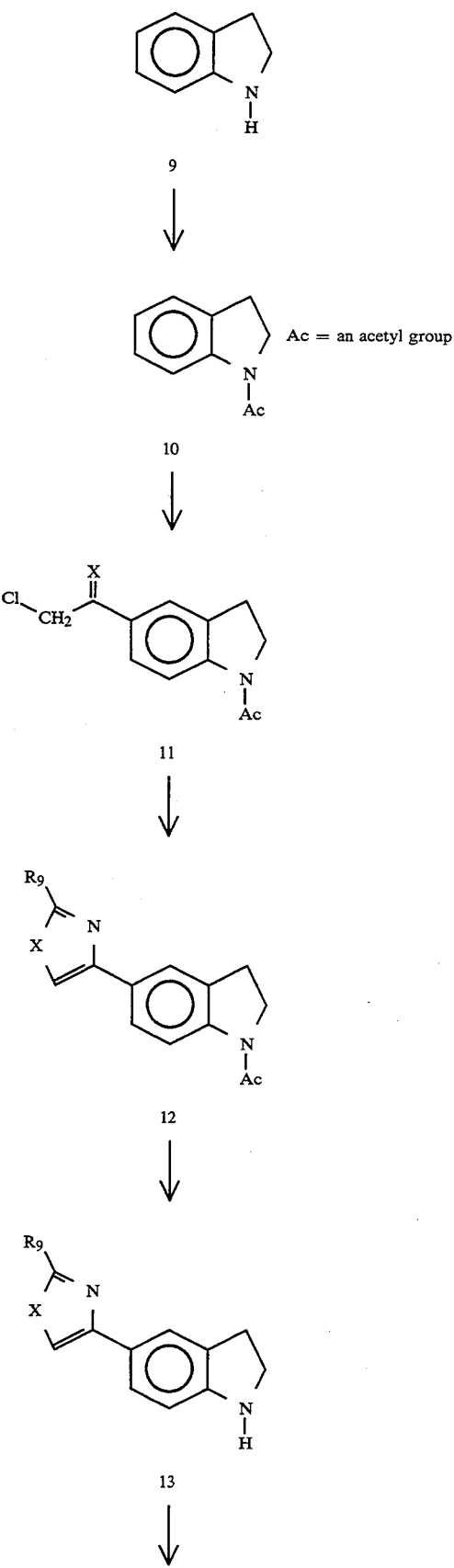

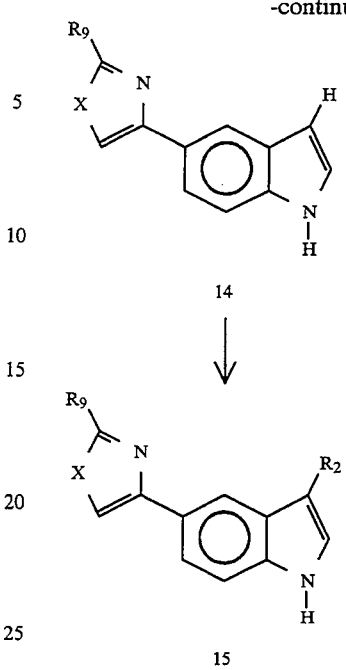

The indoline (9) is reacted with acetyl chloride in the presence of base, preferably triethylamine, to form the 1-acetyl derivative (10). The acetyl moiety acts as a protecting group and other protecting groups which are useful are listed on page 6 of this application. The reaction is carried out in an inert solvent such as methylene chloride, diethyl ether or tetrahydrofuran, preferably methylene chloride, at a temperature of between about 0° C. to about 40° C., preferably about 0° to 5° C. The acetylindoline (10) is converted to keto-indole (11) by its reaction with chloroacetyl chloride in the presence of a Lewis acid such as aluminum chloride or boron trifluoride, preferably the former, in an inert solvent such as benzene, toluene or carbon disulfide. The preferred solvent is carbon disulfide and the temperature of the reaction is from about 25° C. to about 60° C., preferably about 40° C. The thiazole (12) can be prepared by reacting keto-indole compound (11) with an appropriate thioamide to form the thiazole or with an appropriate carboxamide to form the corresponding oxazole. The reactions are conducted in a polar solvent at a temperature between about 20° C. and 100° C., preferably at the reflux temperature of the solvent. Suitable solvents include alcohols, preferably ethanol.

The protecting group is removed from indoline (12) to form the indoline (13) by heating (12) in acidic conditions to a temperature between about 40° C. and 100° C., preferably 50° C. Suitable acids include sulfuric and hydrochloric acids, preferably 6N hydrochloric acid. The solution is then basified with, for example, sodium carbonate or potassium carbonate, preferably the former, to afford (13).

The indole (14) is prepared by treating the indoline (13) with an oxidizing agent such as chloranil or palladium chloride, preferably chloranil. The temperature should be between about 25° C. and 200° C., preferably about 170° C. Suitable solvents include benzene, toluene and xylenes, preferably xylenes.

The compounds (15) are formed as described earlier with regard to compounds (6) and 2A to add substituents at the 3-position. The thiazole (12) can be converted to the thiazole sulfoxide as was described earlier with regard to compound (5).

The 1-substituted compounds are formed by reacting the compounds of the general formula (6) or the reduced form of (4A) with an appropriate alkylating agent in an inert solvent including diethyl ether, methylene chloride or tetrahydrofuran, preferably the latter. The alkylating agents include phenylsulfonyl chloride (forming a —SO$_2$Ph group), acetyl chloride (forming an acetyl group) and iodomethane (forming a methyl group). The reaction is conducted under nitrogen, in a presence of a base such as sodium methoxide, potassium hydride, or sodium hydride, preferably the latter. The reaction temperature should be between about 0° C. and about 25° C., preferably about 5° C.

In order to form the aromatic substituted compounds (8) or (15), an indole (7) or (14) where $R_8$ or $R_9$, respectively, is a chloro-alkyl group is reacted with an appropriate aryl agent in the presence of a base such as sodium or potassium carbonate, preferably sodium carbonate. These aryl reagents include O—, m—, or p— substituted anilines, benzylamine, or an aromatic alcohol such as phenol. The reaction takes place at a temperature of between about 20° C. and about 80° C., preferably about 50° C. A polar solvent, such as ethanol or isopropanol, is used.

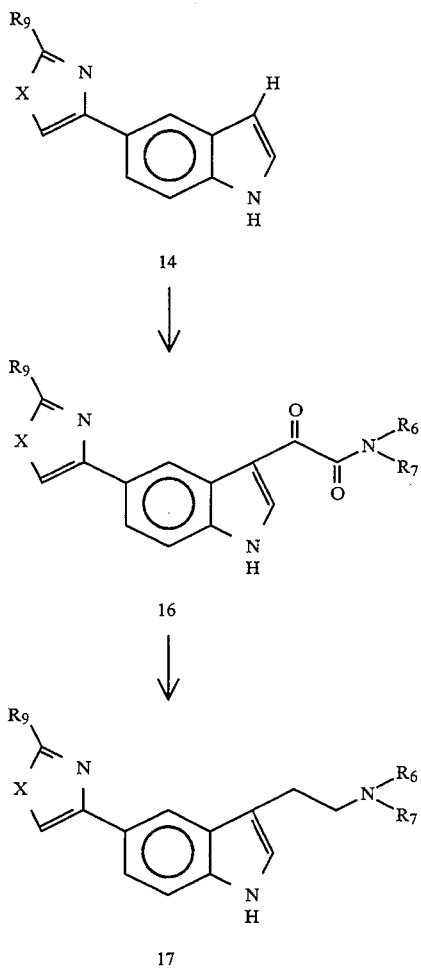

As an alternative, the indoline (14) can be used to first form the dicarbonyl amino substituted indole (16) using a similar procedure as was used to convert cyano indole (1) to indole (2A) described previously. The substituted indole (16) is then reduced to produce the corresponding dialkyl amino substituted form (17) using a similar method to the conversion used to form the dialkyl amino substituted indole (4A), also described previously.

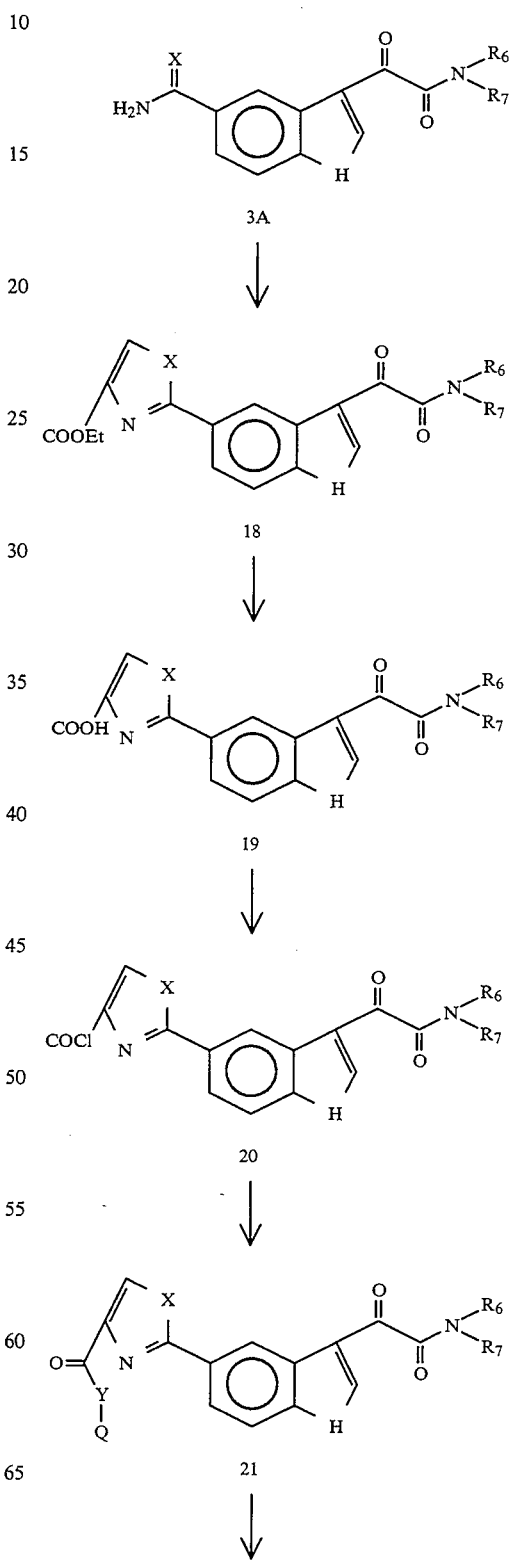

-continued

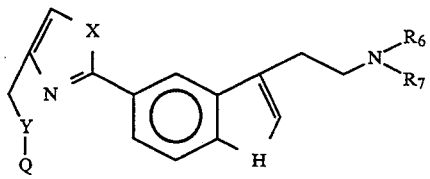

22

The present invention can also be synthesized using the thiocarboxamide or carboxamide (3A) as a starting material. The carboalkoxy thiazole substituted indole (18) is formed by reacting thiocarboxamide or carboxamide (3A) with an appropriate ester of halogenopyruvate, for example, ethyl bromopyruvate to form the carboethoxythiazole substituted compound. The reaction is performed in a polar solvent, such as, for example, ethanol, propanol, isopropanol, tetrahydrofuran, or acetonitrile, preferably ethanol. The reaction temperature should be between about ambient temperature and about 80° C., preferably about the reflux temperature of the solvent used.

The corresponding carboxylic acid derivative (19) is formed by hydrolyzing indole (18) using standard methods known to one skilled in the art.

The acid chloride derivative (20) is synthesized from the carboxylic acid derivative (19) also using methods known to one skilled in the art. The carboxylic acid derivative (19) is then in turn reacted with an appropriate aromatic amine (depending on the desired substituent on the thiazole or oxazole) in a suitable solvent to form the correspond substituted thiazole or oxazole compounds (21). Suitable solvents include methylene chloride, tetrahydrofuran, and benzene, preferably methylene chloride. The reaction temperature should be between about 0° C. and about 80° C., preferably about ambient temperature.

The compounds (21) are then reduced using a similar method as was used for reducing (4A) previously described. The reduction temperature should be between about 20° C. and about 70° C., preferably about 50° C.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful crystallization or evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

The compounds of the formula I and the pharmaceutically acceptable salts thereof (hereinafter, also referred to as the active compounds of the invention) are useful psychotherapeutics and are potent serotonin (5-$HT_1$) agonists and may be used in the treatment of depression, anxiety, eating disorders, obesity, drug abuse, cluster headache, migraine, chronic paroxysmal hemicrania and headache associated with vascular disorders, pain, and other disorders arising from deficient serotonergic neurotransmission. The compounds can also be used as centrally acting antihypertensives and vasodilators.

The active compounds of the invention are evaluated as anti-migraine agents by testing the extent to which they mimic sumatriptan in contracting the dog isolated saphenous vein strip (P. P. A. Humphrey et al., Br. J. Pharmacol., 94, 1128 (1988)). This effect can be blocked by methiothepin, a known serotonin antagonist. Sumatriptan is known to be useful in the treatment of migraine and produces a selective increase in carotid vascular resistance in the anaesthetized dog. It has been suggested (W. Fenwick et al., Br. J. Pharmacol., 96, 83 (1989)) that this is the basis of its efficacy. The active compounds are also evaluated using the method of R. E. Heuring and S. J. Peroutka (J. Neuroscience, 7, 894 (1987)).

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., migraine) is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 $\mu$g to 1000 $\mu$g of the compound of the invention. The overall daily dose with an aerosol will be within the range 100 $\mu$g to 10 mg. Administration may be several times daily, for example 2, 3, 4 or 8 times, giving for example, 1, 2 or 3 doses each time.

The following Preparations illustrate the preparation of starting materials and the following Examples illustrate the preparation of the compounds of the present invention. Melting points are uncorrected. NMR data are reported in parts per million (d) and are referenced to the deuterium lock signal from the sample solvent.

Commercial reagents were utilized without further purification. Chromatography refers to column chromatography performed using 32–63 $\mu$m silica gel and executed under nitrogen pressure (flash chromatography) conditions. Room temperature refers to 20°–25° C.

The compounds of Examples 4A–4D, 7, 8A–8E, 13, 14A–14G, 15A, 15B, 20, 23A–23C, 26 and 28 were evaluated for the 5-HT$_{1D}$ activity using the method developed by R. E. Heuring and S. J. Peroutka (J. Neuroscience, 7, 894 (1987)). All of the compounds had an IC$_{50}$ of at least 1 micromolar. Intermediates are described in Preparations 1–15 and Examples 1A, 1B, 2, 3, 5, 6, 9, 10, 11, 12, 16, 17, 18, 19, 21A–21C, 22A–22C, 24, 25, and 27, 29–32, 34A–34D, 36A–36D, 38A–38B, 39A–39B, and 40A–40B.

PREPARATION 1

1-Phenylsulfonyl-5-cyanoindole

To a stirred solution of 5-cyanoindole (4.26 g, 30 mmol) in anhydrous tetrahydrofuran (75 ml) at room temperature was added portionwise sodium hydride (60% dispersion in mineral oil, 1.24 g, 31 mmol). The resultant mixture was stirred under nitrogen for 1 hours. The dark grey solution was cooled in an ice-bath to about 5° C. and phenylsulfonyl chloride (3.82 ml, 30 mmol) added dropwise at such a rate to maintain the reaction temperature below 15° C. After the addition was complete the ice-bath was removed and stirring at room temperature was continued for 3 hours. The dark brown mixture was then concentrated under reduced pressure. The residual oil was taken up in water (25 ml) and the aqueous mixture extracted with ethyl acetate (2×25 ml). These extracts were combined, dried (MgSO$_4$), and evaporated under reduced pressure. The crude product (a tan solid) was purified by trituration with diethyl ether (25 ml). The product, a white solid was collected by filtration and air dried (7.2 g, 25%). $^1$H NMR (CDCl$_3$) $\delta$=6.69 (d, J=6 Hz, 1H), 7.40–7.58 (m, 4H), 7.66 (d, J=6 Hz, 1H), 7.84 (bs, 2H), 7.86 (s, 1H), 8.04 (d, J=9 Hz, 1H).

PREPARATION 2

1-Phenylsulfonyl-5-thiocarboxamidoindole

A stirred solution of the compound of Preparation 1 (6.9 g, 24.5 mmol) in ethyl acetate (100 ml) was mixed with diethyl dithiophosphate (4.1 ml, 25 mmol). The resultant mixture was saturated with gaseous hydrogen chloride for 15 minutes causing a slight exotherm. After stirring for about 16 hours at room temperature a yellow solid precipitated out of the reaction mixture. The product was collected by filtration, washed with ethyl acetate (25 ml) and air-dried (7.5 g, yield=97%). m.p. 176°–177° C. $^1$H NMR (CDCl$_3$) $\delta$=6.70 (d, J=4 Hz, 1H), 7.38–7.52 (m, 3H), 7.58 (d, J=4 Hz, 1H), 7.72–7.85 (m, 3H), 7.94 (d, J=8 Hz, 1H), 8.08 (s, 1H).

PREPARATION 3

5-Carboxamidoindole

A stirring solution of 5-cyanoindole (2.84 g, 10 mmol) in ethanol (30 ml) was mixed with 30% hydrogen peroxide (10 ml) and stirred under nitrogen for 10 minutes followed by the addition of 3N aqueous NaOH (10 ml). An exotherm was noted and the mixture stirred at room temperature for 6 hours before neutralization with 2N HCl. The resulting mixture was extracted with ethyl acetate (2×50 ml). The combined extracts were washed with aqueous NaHSO$_3$, dried (MgSO$_4$) and concentrated under reduced pressure to afford the title compound (2.4 g, 75% yield) as a white solid. $^1$H NMR (CDCl$_3$) $\delta$=6.62 (bs, 1H), 7.26 (bs, 1H), 7.40 (d, J=6 Hz, 1H), 7.67 (d, J=6 Hz, 1H), 8.13 (bs, 1H).

PREPARATION 4

1-Acetylindoline

To a stirred solution of indoline (1.43 g, 12 mmol) in dry methylene chloride (30 ml) was added triethylamine (1.7 ml, 12.3 mmol). The resultant mixture was cooled in an ice-bath to approximately 5° C. followed by dropwise addition of acetyl chloride (1.77 ml, 12 mmol). After the addition was complete the ice-bath was removed and the mixture was stirred further at room temperature for 1 hour. The reaction mixture was poured onto crushed ice. A methylene chloride extract was separated, washed with brine (20 ml), dried (MgSO$_4$) and evaporated under reduced pressure affording 1.65 g (85% yield) of the title compound as a white solid. $^1$H NMR (CDCl$_3$) δ=2.23 (s, 3H), 3.18 (t, J=6 Hz, 2H), 4.04 (t, J=6 Hz, 2H), 6.96 (t, J=4 Hz, 1H), 7.12–7.20 (m, 2H), 8.18 (d, J=4 Hz, 1H).

PREPARATION 5

1-Acetyl-5-chloracetylindoline

To a stirred solution of the compound of preparation 4 (1.2 g, 7.4 mmol) in carbon disulfide (5 ml) at room temperature was added chloroacetyl chloride (1 ml, 12.5 mmol) followed by a portionwise addition of aluminum chloride (3 g, 22.5 mmol). The resultant mixture was heated at about 40° C. for 5 hours. The upper carbon disulfide layer was decanted, while the dark viscous mass was poured over ice. The obtained tan solid was filtered and air dried. The crude product (1.5 g) was purified by trituration with heptane (30 ml), filtered and air-dried to afford 13 g (74% yield) of the title compound. (J. Gen. Chem., 29, 2835 (1959)) $^1$H NMR (DMSO-d$_6$) δ=2.22 (s, 3H), 3.20 (t, J=4 Hz, 2H), 4.18 (t, J=4 Hz, 2H), 5.12 (s, 2H), 7.84 (s, 1H), 7.86 (d, J=6 Hz, 1H), 8.10 (d, J=6 Hz, 1H).

PREPARATION 6

Indole-5-carboxaldehyde

To a solution of 5-cyanoindole (5 g, 32.2 mmol) in pyridine (70 ml) was added acetic acid (35 ml), an aqueous solution of sodium hypophosphite (10 g in 35 ml H$_2$O) followed by the addition of Ra-Ni. The resultant mixture was heated at 45° C. for 3 hours and then filtered through celite. The filtrate was combined with water (150 ml) and ethyl acetate (150 ml). The organic extract was separated, washed with aqueous cupric sulfate (3×100l ml), water (2×100 ml), dried (MgSO$_4$) and evaporated under reduced pressure to afford 5.1 g of a crude product (a beige solid). The crude product was purified by crystallization from chloroform (40 ml) yielding 2.8 g (55%) of the title compound as a white solid. (Helv. Chim. Acta, 51, 1616 (1968)) $^1$H NMR (CDCl$_3$) δ=6.70 (t, J=2 Hz, 1H), 7.28 (t, J=2 Hz, 1H), 7.46 (d, J=6 Hz, 1H), 7.74 (d, J=6 Hz, 1H), 8.16 (s, 1H). 8.58 (bs, 1H), 9.12 (s, 1H).

PREPARATION 7

5-(1-Ethoxycarbonyloxy)indoleacetonitrile

A solution of the compound of Preparation 6 (2 g, 13.8 mmol) in EtOH (25 ml) was cooled to 0° C. in an ice-bath. To the reaction mixture was added potassium cyanate (1.4, 21 mmol) followed by the dropwise addition of ethyl chloroformate (2.8 g, 26 mmol). As the ethyl chloroformate was added, a white powder precipitated gradually. The reaction mixture was stirred at 0° C. for 90 minutes. The mixture was concentrated under reduced pressure at 20° C. The residual oil was partitioned between methylene chloride (20 ml) and water (20 ml). An organic extract was separated, dried (MgSO$_4$) and evaporated under reduced pressure to afford 2.8 g (83%) of the title compound as a beige solid. (Chem. Pharm. Bull., 20, 2163 (1972)) $^1$H NMR (CDCl$_3$) δ=1.24 (t, J=4 Hz, 3H), 4.18 (m, 2H), 6.28 (s, 1H), 6.52 (m, 1H), 7.16–7.24 (m, 1H), 7.28–7.36 (m, 2H), 7.74 (s, 1H), 8.50 (bs, 1H).

PREPARATION 8

Indole-5-acetonitrile

A mixture of compound of Preparation 7 (2.1 g, 8.6 mmol) and 10% Pd/C in methanol (30 ml) was hydrogenated at 45 psi for 18 hours. The reaction mixture was filtered through celite and the filtrate evaporated under reduced pressure, affording 1.5 g of a crude product as a yellow oil. Purification by flash chromatography of the crude product using silica gel (35 g) and elution with chloroform yielded the title compound (0.85 g, 64%) as a white crystalline solid. $^1$H M (CDCl$_3$) δ=3.80 (s, 2H), 6.44 (m, 1H), 6.98 (d, J=6 Hz, 1H), 7.10–7.16 (m, 1H), 7.26 (d, J=6 Hz, 1H), 7.48 (s, 1H), 8.34 (bs, 1H).

PREPARATION 9

1-Phenylsulfonylindole-5-acetonitrile

Procedure identical to Example 1. The reagents used include the compound of Preparation 8 (0.73 g, 4.7 mmol), sodium hydride (0.25 g, 5.1 mmol), phenylsulfonyl chloride (0.6 ml, 4.7 mmol), tetrahydrofuran (50 ml). Yield: 0.55 g (40%) of the title compound as a beige solid. $^1$H NMR (CDCl$_3$) δ=3.80 (s, 2H), 6.44 (d, J=2 Hz, 1H), 7.20 (dd, J$_1$=2 Hz, J$_2$=6 Hz, 1H), 7.38–7.44 (m, 4H), 7.58 (d, J=2 Hz, 1H), 7.84 (d, J=6 Hz, 2H), 7.96 (d, J=6 Hz, 1H).

PREPARATION 10

1-Phenylsulfonyl-5-thioacetamidoindole

Procedure as described in Example 2. The reagents used include the compound of Preparation 9 (0.35 g, 1.2 mmol), diethyl dithiophosphate (0.2 ml, 1.2 mmol) and ethyl acetate (30 ml). Yield: 0.27 g (68%) of the title compound as a yellow solid. $^1$H NMR (CDCl$_3$) δ=4.48 (s, 2H), 6.70 (d, J=2 Hz, 1H), 7.37–7.44 (m, 2H), 7.50 (d, J=6 Hz, 1H), 7.60 (d, J=2 Hz, 1H), 7.74–7.86 (m, 3H), 7.96 (d, J=6 Hz, 1H), 8.10 (s, 1H).

PREPARATION 11

5-Cyano-3-(1-methyl-1,2,5,6-tetrahydropyrid-4-yl)indole

Procedure identical to Example 4. The reagents used include 5-cyanoindole (10 g, 70.4 mmol), 1-methyl-4-piperidone (8.65 ml, 70.4 mmol), sodium (3.45 g, 0.15 mmol) and methanol (200 ml). Reflux time was 48 hours. An orange solution was allowed to cool down to room temperature and concentrated under reduced pressure to ∼100 ml volume. Product crystallized out of the methanolic solution as a beige solid, was collected by filtration and air-dried to afford 14.1 g (80.5%) of the title compound. $^1$H NMR (CDCl$_3$) δ=2.44 (s, 3H), 2.52 (bs, 2H), 2.68 (t, J=4 Hz, 2H), 3.12–3.22 (m, 2H), 6.08 (bs, 1H), 7.12 (s, 1H), 7.32 (bs, 2H), 8.12 (s, 1H).

PREPARATION 12

5-Cyano-3-(1-methylpiperidin-4-yl)indole

A suspension of the compound of Preparation 11 (10 g, 30.5 mmol) and 10% palladium on carbon catalyst (1 g) in ethanol (150 ml) was hydrogenareal at 45 psi for 36 hours. The reaction mixture was filtered through celite and the filtrate evaporated under reduced pressure. Purification of the crude-product by flash chromatography using silica gel (200 g) and elution with chloroform-methanol (10:1) yielded the title compound (8.85 g, 68%) as a tan solid. $^1$H NMR (CD$_3$OD) δ=1.70 (dd, J$_1$2 Hz, J$_2$=6 Hz, 2H), 1.95 (d, J=6 Hz, 2H), 2.18 (t, J=6 Hz, 2H), 2.30 (s, 3H), 2.70–2.85 (m, 1H), 4.95 (s, 1H), 7.15 (s, 1H), 7.32 (d, J=4 Hz, 1H), 7.42 (d, J=4 Hz, 1H), 8.03 (s, 1H).

PREPARATION 13

3-(1-Methylpiperidin-4-yl)-5-(thiocarboxamido)indole

Procedure identical to Preparation 2. The reagents used include the compound of Preparation 12 (5.05 g, 17.7 mmol), diethyl dithiophosphate (2.97 ml, 17.7 mmol) and ethyl acetate (100 ml). Reaction time was 48 hours. Product precipitated out of the ethyl acetate solution was collected by filtration, washed with ethyl acetate (2×20 ml) and air-dried yielding 6.1 g (93%) of the title compound as an orange solid. $^1$H NMR (CDCl$_3$) δ=1.80–1.85 (m, 2H), 1.98 (d, J=6 Hz, 2H), 2.08 (t, J=6 Hz, 2H), 2.32 (s, 3H), 2.74–2.84 (m, 1H), 2.88 (d, J=6 Hz, 2H), 6.98 (s, 1H), 7.28 (d, J=6 Hz, 1H), 7.36 (s, 1H), 7.48–7.58 (m, 1H), 7.74 (d, J=6 Hz, 1H), 8.24 (bs, 1H).

PREPARATION 14

2[3-(N,N-Dimethylglyoxamid)indol-5-yl]-4-(carboethoxy) thiazole

To a suspension of the compound of Example 10 (9 g, 32.7 mmol) in ethanol (100 ml) was added dropwise ethyl bromopyruvate (4.1 ml, 32.7 mmol). The resultant mixture was heated at refluxed temperature for 8 hours. A product started to precipitate out of the ethanolic solution after 2 hours of reflux. The reaction mixture was allowed to reach ambient temperature before the product was isolated by filtration. The crude product (8.1 g) was purified by trituration with chloroform (25 ml) followed by filtration and air-drying to afford 7.4 g (61%) of the title compound as a beige solid. $^1$H NMR (CDCl$_3$) δ=1.41 (s, 6 Hz, 3H), 3.04 (s, 3H), 3.08 (s, 3H), 4.43 (J=6 Hz, 2H), 7.27 (d, J=8 Hz, 1H), 7.86 (dd, J$_1$=6 Hz, J$_2$=3 Hz, 1H), 7.92 (d, J=3 Hz, 1H), 8.13 (s, 1H), 8.77 (s, 1H).

PREPARATION 15

2[3-(N,N-Dimethylglyoxamid)indol-5-yl]-4-carboxylic acid

A mixture of the compound of Preparation 14 (7 g, 18.9 mmol) and 100 ml of 3N aq. KOH was stirred at ambient temperature for 16 hours. An orange solution was cooled to ~5° C. and acidified with 6N HCl to pH=5. The product precipitated out of the aqueous solution was collected by filtration and dried to afford 5.58 g (86%) of the title compound as a white solid. $^1$H NMR (DMSO) δ=2.97 (s, 3H), 3.04 (s, 3H), 7.66 (d, J=8Hz, 1H), 7.91 (d, J=8 Hz, 1H), 8.24 (s, 1H), 8.46 (s, 1H), 8.74 (s, 1H).

EXAMPLE 1

General Procedure for the Synthesis of 2-(1-phenylsulfonylindol-5-yl)thiazole

A stirred solution of the compound of Preparation 2 (0.95 g, 3 mmol) in absolute ethanol (20 ml) was mixed with the appropriate α-chlorocarbonyl reactant (6 mmol, 2 eq) and heated at reflux for 3–5 hours. The reaction mixture was then cooled and concentrated under reduced pressure. The residual oil or solid was either triturated with ether or column chromatographed yielding the desired product.

1A. 2-(1-Phenylsulfonylindol-5-yl)thiazole

The α-chlorocarbonyl reactant was 50% aqueous chloroacetaldehyde and the reaction time was 5 hours. Purification by flash chromatography of the crude product using silica gel (60 g) and elution with hexanes-ethyl acetate (50:50) yielded the title compound (0.89 g, 85% yield) as a yellow solid. $^1$H NMR (CDCl$_3$) δ=6.70 (d, J=4 Hz, 1H), 7.28 (d, J=4 Hz, 1H), 7.40–7.53 (m, 3H), 7.59 (d, J=4 Hz, 1H), 7.82 (d, J=4 Hz, 1H), 7.85–7.90 (m, 3H), 7.90–8.05 (m, 1H), 8.11 (bs, 1H). Low Resolution Mass Spectroscopy, 340 (M+, 88).

1B. 2-(1-Phenylsulfonylindol-5-yl)-4-methylthiazole

The α-chlorocarbonyl reactant was chloroacetone. The reaction time was 3 hours. Crystalline product started to precipitate out of the reaction mixture after 2 hours of reflux. The product was collected by filtration, triturated with ether (15 ml) and air-dried to produce a light yellow solid (0.92 g, 87% yield), m.p. 209–210° C. $^1$H NMR (CDCl$_3$) δ=6.84 (d, J=4 Hz, 1H), 7.06 (bs, 1H), 7.38–7.46 (m, 2H), 7.50–7.56 (m, 1H), 7.62 (d, J=4 Hz, 1H), 7.84 (m, 2H), 8.00–8.10 (m, 2H), 8.62 (bs, 1H). Low Resolution Mass Spectroscopy; 354 (M+, 54).

EXAMPLE 2

2-(1-Phenylsulfonylindol-5-yl)-1-oxothiazole (compound 4)

To a stirred solution of the compound of Example 1A (0.5 g, 1.5 mmol) in methylene chloride (20 ml) was added a solution of m-chloroperbenzoic acid (0.63 g, 3.7 mmol, 2.5 eq) in methylene chloride (5 ml). The mixture was stirred under nitrogen at ambient temperature for 36 hours. Product precipitated as a white, fine solid, and was filtered, washed with methylene chloride (5 ml) and air-dried (0.3 g, yield=57%). $^1$H NMR (CDCl$_3$) δ=6.72 (d, J=4 Hz, 1H), 7.22 (d, J=4 Hz, 1H), 7.36–7.55 (m, 3H), 7.60 (d, J=4 Hz, 1H), 7.74 (d, J=4 Hz, 1H), 7.85 (dd, J$_1$=2 Hz, J$_2$=6 Hz, 2H), 7.94–8.00 (m, 2H), 8.76 (bs, 1H). Low Resolution Mass Spectroscopy; 356 (M+, 20).

EXAMPLE 3

2-(Indol-5-yl)-4-methyloxazole

Chloroacetone (1.6 ml, 20 mmol) was added to a stirred solution of the compound of Preparation 3 (2 g, 12.5 mmol) in absolute ethanol (40 ml) and heated at reflux under nitrogen for 7 hours. Upon cooling the reaction mixture was evaporated under reduced pressure. The residual oil was dissolved in ethyl acetate (50 ml) and washed with aqueous sodium bicarbonate, dried (MgSO$_4$) and concentrated under reduced pressure to yield an oil. Column chromatography of this oil using silica gel (50 g) and elution with chloroform afforded the title compound (1.1 g, 44%) as a white solid $^1$H NMR (CDCL$_3$) δ=6.58 (bs, 1H) 7.18–7.24 (m, 1H) 7.34–7.40 (m, 2H), 7.86 (dd, J$_1$=2 Hz, J$_2$=6 Hz, 1H), 8.30 (bs, 1H). Low Resolution Mass Spectroscopy; 198 (M+, 92).

EXAMPLE 4

General Procedure For The Synthesis Of 2-[3-(1,2,5,6-Tetrahydropyrid-4-yl)-indol-5-yl]thiazole (oxazole) compounds Part (a)—A solution of sodium methoxide was prepared by the addition of sodium (0.14 g, 6 mmol), 4 eg.

to methanol (20 ml) under nitrogen. This solution was mixed with the appropriate thiazole (oxazole) derivative (1.5 mmol) and stirred at room temperature for 30 minutes followed by the addition of N-t-BOC-4-piperidone (0.6 g, 3 mmol, 2, eq) in methanol (5 ml). The resulting mixture was heated at reflux for 3–8 hours depending on the thiazole (oxazole) substrate, cooled and then concentrated under reduced pressure. The residue (oil or solid) was column chromatographed yielding the desired intermediate.

Part (b)—Removal of the protecting group with methanolic HCl yielded the final product.

4A. (a) 2-[3-(tert-Butoxycarbonyl-1,2,5,6-tetrahydropyrid-4-yl)indol-5-yl]thiazole The reaction time was 3 hours. Purification by flash chromatography of the crude product using silica gel (30 g) and elution with chloroform-methanol (30:1) yielded the title compound (0.56 g, 98% yield) as a colorless thick oil. $^1$H NMR (CDCl$_3$) δ=1.48 (s, 9H), 2.54 (bs, 2H), 3.65 (t, J=4 Hz, 2H), 4.15 (bs, 2H), 6.18 (bs, 1H), 7.16 (d, J=2 Hz, 1H), 7.24 (s, 1H), 7.35 (d, J=6 Hz, 1H), 7.75 (d, J=6 Hz, 1H), 7.80 (d, J=2 Hz, 1H), 8.45 (bs, 1H).

(b) 2-[3-(1,2,5,6-Tetrahydropyrid-4-yl)-indol-5-yl]thiazole

The reaction time was 90 minutes. The reaction mixture was concentrated under reduced pressure. The residual oil was taken up in water (5 ml), basified with 3N NaOH to pH=10 and the aqueous mixture extracted with ethyl acetate (5×20 ml). These extracts were combined, dried (MgSO$_4$), and evaporated under reduced pressure. The crude product was triturated with CHCl$_3$ (10 ml). The product, a tan solid, was collected by filtration and air-dried (0.15 g, 36% yield) m.p. 183–185° C. $^1$H NMR (CDCl$_3$) δ=2.42 (bs, 2H), 3.08 (t, J=4 Hz, 2H), 3.52 (bs, 2H), 6.14 (bs, 1H), 7.10 (s, 1H), 7.20 (d, J=2 Hz, 1H), 7.30 (d, J=6 Hz, 1H), 7.72 (d, J=6 Hz, 1H), 7.80 (d, J=2 Hz, 1H), 8.48 (bs, 1H). Low Resolution Mass Spectroscopy; 281 (M+, 100).

4B. (a) 2[3-(1-tert-Butoxycarbonyl-1,2,5,6-tetrahydropyrid-4-yl)indol-5-yl)]-4-methylthiazole The reaction time was 4 hours. Purification by flash chromatography of the crude product using silica gel (30 g) and elution with chloroform yielded the title compound (0.45 g, 76% yield) as a beige solid. $^1$H NMR (DMSO-d$_6$) δ=1.90 (bs, 9H), 2.42 (s, 3H), 3.38 (bs, 2H), 3.80 (bd, 2H), 5.04 (s, 1H), 7.14 (s, 1H), 7.24 (bs, 1H), 7.38 (d, J=6 Hz, 1H), 7.58 (d, J=6 Hz, 1H), 8.34 (bs, 1H).

(b) 2-[3-(1,2,5,6-Tetrahydropyrid-4-yl)-indol-5-yl]-4-methylthiazole

The reaction time was 2 hours. The reaction mixture was concentrated under reduced pressure. The residual oil was taken up in water (5 ml), basified with 3N NaOH to pH=10 and the aqueous mixture extracted with ethyl acetate (5×20 ml). These extracts were combined, dried (MgSO$_4$), and evaporated under reduced pressure. Purification by flash chromatography of the crude product using silica gel (25 g) and elution with 5% triethylamine in methanol yielded the title compound (0.12 g, 27%) as a yellow solid. $^1$H NMR (CDCl$_3$) δ=2.48 (s, 3H), 2.68 (m, 2H), 3.38 (t, J=6 Hz, 2H), 3.78 (bs, 2H), 6.00 (bs, 1H), 7.16 (s, 1H), 7.24 (bs, 1H), 7.36 (d, J=6 Hz, 1H), 7.60 (d, J=6 Hz, 1H), 8.30 (s, 1H). Low Resolution Mass Spectroscopy: 295 (M+, 100).

4C. (a) 2-[3-(1-Tert-butoxycarbonyl-1,2,5,6-tetrahydropyrid-4-yl)indol-5-yl]-1-oxothiazole The reaction time was 5 hours. Purification by flash chromatography of the crude product using silica gel (30 g) and elution with chloroform-methanol (15:1) yielded the title compound (0.53 g, 45%) as a colorless oil. $^1$H NMR (CDCl$_3$) δ=1.44 (s, 9H), 2.32–2.46 (m, 2H), 3.60 (t, J=4 Hz, 2H), 4.08 (bs, 2H), 6.12 (bs, 1H), 6.96 (bs, 1H), 7.08 (d, J=2 Hz, 1H), 7.28 (d, J=2 Hz, 1H), 7.68 (d, J=2 Hz, 1H), 9.82 (bs, 1H).

(b) 2-[3-(1,2,5,6-Tetrahydropyrid-4-yl)indol-5-yl]-1-oxothiazole

The reaction time was 3 hours. The reaction mixture was concentrated under reduced pressure. The residual oil was taken up in methanol (10 ml), basified with triethylamine and then evaporated under reduced pressure. Purification by flash chromatography of the crude product using silica gel (20 g) and elution with triethylamine-methanol. (5:95 yielded the title compound (0.2 g, 66%) as a light yellow solid. $^1$H NMR (CD$_3$OD) δ=2.57 (bs, 2H), 3.10 (t, J=6 Hz, 2H), 3.56 (bs, 2H), 6.30 (bs, 1H), 7.40 (s, 1H), 7.50 (d, J=8 Hz, 1H), 7.70 (d, J=2 Hz, 1H), 7.78 (d, J=8 Hz, 1H), 7.81 (d, J=2 Hz, 1H), 9.12 (bs, 1H). Low Resolution Mass Spectroscopy: 297 (M+, 10).

4D (a) 2-[3-1-tert-Butoxycarboxyl-1,2,5,6-tetrahydropyrid-4-yl) indol-5-yl]-4-methyloxazole The reaction time was 8 hours. Purification by flash chromatography of the crude product using silica gel (30 g) and elution with hexanes-ethyl acetate (1:1) to yield the title compound (0.21 g, 37%) as a yellow solid. $^1$H NMR (CDCl$_3$) δ=1.50 (s, 9H), 2.16 (s, 3H), 2.54 (bs, 2H), 3.66 (t, J=4 Hz, 2H), 4.12 (bs, 2H), 6.20 (bs, 1H), 7.18 (d, J=2 Hz, 1H), 7.36 (d, J=2 Hz, 1H), 7.38 (d, J=6 Hz, 1H), 7.88 (d, J=6 Hz, 1H), 8.52 (bs, 1H).

(b) 2-[3-(1,2,5,6-Tetrahydropyrid-4-yl)indol-5-yl]-4-methyloxazole

The reaction time was 4 hours. The reaction mixture was concentrated under reduced pressure. The residual solid was taken up in methanol (15 ml), basified with triethylamine and finally evaporated under reduced pressure. Column chromatography of the crude product using silica gel (30 g) and elution with triethylamine-methanol (5:95) afforded the title compound (84 mg, 20%) as a beige solid. $^1$H NMR (CDCl$_3$) δ=2.26 (s, 3H), 2.46 (bs, 2H), 3.12 (t, J=6 Hz, 2H), 3.58 (bs, 2H), 6.30 (bs, 1H), 7.34 (d, J=6 Hz, 1H), 7.38 (d, J=2 Hz, 1H), 7.86 (d, J=6 Hz, 1H), 8.52 (s, 1H). Low Resolution Mass Spectroscopy 279 (M +, 100). High resolution Mass Spectroscopy: calculated for C$_{12}$H$_{17}$N$_3$O: 279.13415; found 279.1361.

EXAMPLE 5

2-(Indol-5-yl)thiazole

A solution of the compound of Example 1A (3.8 g, 11.2 mmol) in methanol (50 ml) was stirred with solid potassium carbonate (2.7 g, 20 mmol) and heated at 50° C. for 2.5 hrs. Upon cooling, insolubles were filtered off and the filtrate was concentrated under reduced pressure. The residual light brown solid was dissolved in chloroform (30 ml), washed with water, dried (MgSO$_4$) and concentrated under reduced pressure to afford the title compound as a yellow solid (1.5 g, 71.2%). $^1$H NMR (CDCl$_3$) δ=6.60 (bs, 1H), 7.20 (t, J=3 Hz, 1H), 7.24 (d, J=3 Hz, 1H), 7.78–7.86 (m, 2H), 8.24 (s, 1H), 8.72 (bs, 1H).

EXAMPLE 6

2-[3-(N,N-Dimethylglyoxamid)indol-5-yl]thiazole

Oxalyl chloride (0.96 ml, 10 mmol) was added to a stirring mixture of the compound of Example 5 (0.74 g, 4 mmol) and phthalimide (0.24 g, 1.6 mmol) in dry ethyl ether (25 ml). The reaction mixture was stirred at room temperature for 2 hours. The yellow suspension was then carefully saturated with anhydrous dimethylamine. Product precipitated out of reaction mixture as a white solid. The product was collected by filtration, washed with ethyl ether (20 ml) and air-dried (0.6 g, 50%). $^1$H NMR (CDCl$_3$) $\delta$=2.66 (s, 6H), 7.22 (s, 1H), 7.28 (s, 1H), 7.44 (d, J=6 Hz, 1H), 7.82 (s, 1H), 7.88–7.98 (m, 2H), 8.82 (bs, 1H).

EXAMPLE 7

2-[3-(N,N-Dimethylaminoethyl)indol-5-yl]thiazole

To a slurry of lithium aluminum hydride (0.11 g, 3 mmol) in dry tetrahydrofuran (10 ml) was added under nitrogen a solution of the compound of Example 6 (0.18 g, 0.6 mmol) in tetrahydrofuran (5 ml). The resultant mixture was refluxed for 3 hours, then cooled, quenched with aqueous sodium sulfate. The resultant suspension was filtered through celite and the filtrate concentrated to dryness under reduced pressure. Purification by flash chromatography of the crude product using silica gel (3 g) and elution with chloroform-methanol (10:1) yielded the title compound (50 mg, 31%) as a beige solid. $^1$H NMR (CDCl$_3$) $\delta$=2.32 (s, 6H), 2.66 (t, J=6 Hz, 2H), 2.86 (t, J=6 Hz, 2H), 6.98 (s, 1H), 7.22 (d, J=3 Hz, 1H), 7.28 (d, J=6 Hz, 1H), 7.92 (d, J=6 Hz, 1H), 7.78 (d, J=3 Hz, 1H), 8.18 (s, 1H), 8.54 (bs, 1H). Low Resolution Mass Spectroscopy 271 (M+, 5).

EXAMPLE 8

General Procedure for the Synthesis of 2-[1-substituted-3-(1,2,5,6-tetrahydropyrid-4-yl)-indol-5-yl]thiazoles Part (a)—To a stirred solution of the compound of Example 4A or 4B (0.5 mmol) in anhydrous tetrahydrofuran (5 ml) under nitrogen was added sodium hydride (24 mg, 1 mmol). The resultant suspension was stirred at room temperature for 1 hour, then cooled in an ice-bath to approximately 5° C. followed by addition of an appropriate alkylating reagent (0.51 mmol). After the addition was complete the ice-bath was removed and the mixture was stirred further at room temperature for 1–2 hours depending on the alkylating agent. The dark brown mixture was quenched with H$_2$O (20 ml) and the aqueous solution extracted with ethyl acetate (10 ml). The ethyl acetate extract was washed with brine (3×10 ml), dried (MgSO$_4$) and evaporated under reduced pressure affording the desired intermediate.

Part (b)—Removal of the protecting group with methanolic HCl yielded the final product.

8A. (a) 2-[1-Acetyl-3-(1-tert-butoxycarbonyl-1,2,5,6-tetrahydropyrid-4-yl)indol-5-yl]thiazole The starting materials were the compound of Example 4A and acetyl chloride. The reaction time was 1 hour. The title compound was isolated as a brown oil (0.15 g, 70%). $^1$H NMR (CDCl$_3$) $\delta$=1.45 (s, 9H), 2.50 (m, 2H), 2.60 (s, 3H), 3.64 (t, J=6 Hz, 2H), 4.12 (m, 2H), 6.26 (bs, 1H), 7.20 (s, 1H), 7.28 (d, J=3 Hz, 1H), 7.30 (bs, 1H), 7.80–7.86 (m, 2H), 8.36 (s, 1H) 8.46 (bs, 1H).

(b) 2-[1-Acetyl-3-(1,2,5,6-tetrahydropyrid-4-yl)indol-5-yl]thiazole

The reaction time was 4 hours. The reaction mixture was concentrated under reduced pressure. The residual oil was taken up in water (5 ml), basified with aqueous solution of sodium bicarbonate and the aqueous mixture extracted with ethyl acetate (5×5 ml). The extracts were combined, dried (MgSO$_4$) and evaporated under reduced pressure. Purification by flash chromatography of the crude product using silica gel (5 g) and elution with methanol-TEA (95:5) yielded the title compound (65 mg, 38%) as a light yellow solid. $^1$H NMR (CDCl$_3$) $\delta$=2.26 (m, 2H), 2.28 (s, 3H), 3.16 (t, J=6 Hz, 2H), 3.58 (m, 2H), 6.30 (bs, 1H), 7.16 (s, 1H), 7.24 (s, 1H), 7.36 (d, J=8 Hz, 1H), 7.76 (d, J=8 Hz, 1H), 7.80 (d, J=3 Hz, 1H), 8.48 (bs, 1H), 8.98 (m, 1H). Low Resolution Mass Spectroscopy: 280 (M+-COCH$_3$, 36).

8B. (a) 2-[1-Ethoxycarbonyl-3(1-tert-butoxycarbonyl-1,2,5,6-tetrahydropyrid-4-yl]indol-5-yl]thiazole The substrates were the compound of Example 4A and ethyl chloroformate. The reaction time was 2 hours. The title compound was isolated as a yellow oil (0.2 g, 92%). $^1$H NMR (CDCl$_3$) $\delta$=0.82 (t, J=6 Hz, 3H), 1.40 (s, 9H), 2.50 (m, 2H), 3.62 (t, J=4 Hz, 2H), 4.10 (m, 2H), 4.46 (d, J=6 Hz, 2H), 6.26 (bs, 1H), 7.02 (s, 1H), 7.28 (d, J=3 Hz, 1H), 7.52 (s, 1H), 7.80 (d, J=3 Hz, 1H), 7.84 (d, J=6 Hz, 1H), 8.18 (d, J=6 Hz, 1H), 8.36 (s, 1H).

(b) 2-[1-Ethoxycarbonyl-3-(1,2,5,6-tetrahydropyrid-4-yl) indol-5-yl]thiazole

The reaction time was 3.5 hours. The reaction mixture was concentrated under reduced pressure. The residual oil was taken up in water (5 ml), basified with an aqueous solution of sodium bicarbonate, extracted with ethyl acetate (5×5 ml). The organic extracts were combined, dried (MgSO$_4$) and evaporated under reduced pressure. Purification by flash chromatography of-the crude product using silica gel (3 g) and elution with methanol-TEA (95:5) afforded the title compound (52 mg, 29%) as a yellow solid. $^1$H NMR (CDCl$_3$) $\delta$=1.42 (t, J=6 Hz, 3H), 2.42 (m, 2H), 3.10 (t, J=6 Hz, 2H), 3.56 (m, 2H), 4.44 (q, J=6 Hz, 2H), 6.35 (bs, 1H), 7.20 (s, 1H), 7.26 (d, J=3 Hz, 1H), 7.50 (s, 1H), 7.80 (d, J=3 Hz, 1H), 7.84 (d, J=6 Hz, 1H), 8.20 (d, J=6 Hz, 1H), 8.38 (s, H). Low Resolution Mass Spectroscopy: 353 (M+, 100).

8C. (a) 2-[1-Phenylsulfonyl-3-(1-tert-butoxycarbonyl-1,2,5,6-tetrahydropyrid-4-yl)indol-5-yl]-4-methylthiazole The substrates were the compound of Example 4B and phenylsulfonyl chloride. The reaction time was 2 hours. The title compound was isolated as a yellow solid (0.26 g, 98%). $^1$H NMR (DMSO-d$_6$) $\delta$=1.46 (s, 9H), 2.42 (s, 3H), 2.80 (m, 2H), 3.35 (m, 2H), 3.80 (m, 2H), 6.30 (bs, 1H), 7.34 (s, 1H), 7.60 (t, J=6 Hz, 2H), 7.70 (t, J=6 Hz, 1H), 7.90 (d, J=6 Hz, 1H), 8.06 (m, 4H), 8.28 (s, 1H), 9.30 (bs, 1H).

(b) 2-[1-Phenylsulfonyl-3-(1,2,5,6-tetrahydropyrid-4-yl)indol-5-yl]-4-methylthiazole The reaction time was 2 hours. The reaction mixture was concentrated under reduced pressure and the residual yellow oil triturated with methanol (2 ml). A tan solid crystallized out and was collected by filtration and air-dried affording the title compound as a hydrochloride salt (92 mg, 40%). M.p. 252–254° C. $^1$H NMR (DMSO-d$_6$) $\delta$=2.40 (s, 3H), 2.80 (m, 2H), 3.35 (m, 2H), 3.82 (m, 2H), 6.30 (bs, 1H), 7.32 (s, 1H), 7.60 (t, J=6 Hz, 2H), 7.72 (t, J=6 Hz, 1H), 7.90 (d, J=6 Hz, 1H), 8.06

(m, 4H), 8.28 (s, 1H), 9.30 (bs, 1H). Low Resolution Mass Spectroscopy: 435 (M+, 10).

8D. (a) 2-[1-Methyl-3(1-tert-butoxycarbonyl-1,2,5,6-tetrahydropyrid-4-yl)indol-4-yl]-4-methylthiazole The starting materials were the compound of Example 4B and iodomethane. The reaction time was 1 hour. The title compound was isolated as a yellow foam (0.1 g, 87%). $^1$H NMR (CDCl$_3$) δ=1.50 (s, 9H), 2.50 (s, 3H), 2.5.2 (m, 2H), 3.66 (t, J=6 Hz, 2H), 3.74 (s, 3H), 4.14 (m, 2H), 6.16 (bs, H), 6.78 (s, 1H), 7.00 (s, 1H), 7.24 (t, J=6 Hz, 1H), 7.78 (d, J=6 Hz, 1H), 8.38 (bs, 1H).

(b) 2-[1-Methyl-3-(1,2,5,6-tetrahydropyrid-4-yl)indol-5-yl]-4-methylthiazole

The reaction time was 3 hours. The reaction mixture was evaporated under reduced pressure and crude product crystallized upon trituration with methanol (2 ml). The yellow crystalline product of the title compound, a hydrochloride salt, was collected by filtration and air-dried (31 mg, 60%). m.p. 297–299° C. decomp. $^1$H NMR (DMSO) δ=2.44 (s, 3H), 2.72 (m, 2H), 3.38 (m, 2H), 3.84 ( s, 3H), 3.86 (m, 2H), 6.18 (bs, 1H), 7.24 (S, 1H), 7.56 (d, J=6 Hz, 1H), 7.62 (s, 1H), 7.76 (d, J=6 Hz, 1H), 8.35 (s, 1H), 9.06 (m, 1H). Low Resolution Mass Spectroscopy: 309 (M+, 90).

8 E. (a) 2-[1-Benzyl-3-(1-tert-butoxycarbonyl-1,2,5,6-tetrahydropyrid-4-yl)indol-5-yl]-4-methylthiazole The substrates were the compound of Example 4B and benzyl bromide. The reaction time was 1.5 hours. The title compound was isolated as .a yellow solid (0.24 g, 90%). $^1$H NMR (CDCl$_3$) δ=1.48 (s, 9H), 2.48 (s, 3H), 2.50 (m, 2H), 3.62 (t, J=3 Hz, 2H), 4.12 (m, 2H), 4.45 (s, 2H), 6.18 (bs, 1H), 7.05 (m, 2H), 7.20–7.36 (m, 6H), 7.70 (d, J=6 Hz, 1H), 8.40 (s, 1H).

(b) 2-[1-Benzyl-3-(1,2,5,6-tetrahydropyrid-yl)indol-5-yl]-4-methylthiazole

The reaction time was 3.5 hours. The reaction mixture was concentrated under reduced pressure. The crude product was purified by trituration with methanol (2 ml). The yellow crystalline product compound was collected by filtration and air-dried (0.12 g, 71%). m.p. 299–301° C. decomp. $^1$H NMR (DMSO-d$_6$) δ=2.43 (s, 3H), 2.74 (m, 2H), 3.36 (m, 2H), 3.84 (m, 2H), 3.98 (bs, 2H), 6.20 (bs, 1H), 7.20–7.32 (m, 6H), 7.40 (d, J=6 Hz, 1H), 7.50 (d, J=6 Hz, 1H), 7.82 (s, 1H), 8.36 (s, 1H), 9.04 (bs, 1H). Low Resolution Mass Spectroscopy: 385 (M+, 45).

EXAMPLE 9

5-Cyano-3-(N,N-dimethylglyoxamido)indole

Oxalyl chloride (9.16 ml, 105 mmol) was added to a stirring mixture of 5-cyanoindole (10 g, 70.4 mmol) and phthalimide (4.14 g, 28.1 mmol) in dry ethyl ether (150 ml). The reaction mixture was stirred at room temperature for 18 hours. The yellow suspension was then carefully saturated with anhydrous dimethylamine. Product precipitated out of reaction mixture as a white solid. The product was collected by filtration washed with ethyl ether (30 ml) and air dried (12.6 g, 75%). $^1$H NMR (CDCl$_3$) δ=3.06 (s, 3H), 3.10 (s, 3H), 7.38 (d, J=3 Hz, 1H), 7.44 (d, J=3 Hz, 1H), 8.60 (s, 1H).

EXAMPLE 10

3-(N,N-Dimethylglyoxamid)-5-(thiocarboxamidolindole

A stirred solution of the compound of Example 9 (9 g, 37.3 mmol) in ethyl acetate (200 ml) was mixed with diethyl dithiophosphate (6.26 ml, 37.3 mmol). The resultant mixture was saturated with gaseous hydrogen chloride for 15 minutes causing a slight exotherm (reaction temperature rose to 40° C). The reaction mixture was allowed to cool down to room temperature before it was resaturated with hydrogen chloride (for about 10 minutes, reaction temperature rose again to 40° C.). After stirring for 4 days at room temperature a yellow solid precipitated out of the reaction mixture. The title compound was collected by filtration, washed with ethyl acetate (30 ml) and air-dried (0.1 g, 88.5%). $^1$H NMR (CDCl$_3$) δ=3.04 (s, 1H), 3.07 (s, 1H), 7.38 (d, J=3 Hz, 1H), 7.44 (d, J=3 Hz, 1H). 7.88 (d, J=1.5 Hz, 1H), 8.42 (bs, 1H). Low Resolution Mass Spectroscopy: 275 (M+, 10).

EXAMPLE 11

2-[3-(N,N-Dimethylglyoxamid)indol-5-yl]-4-(chloromethyl)thiazole

To a suspension of the title compound of Example 10 (8 g, 2.9 mmol) in isopropyl alcohol (150 ml) was added 1,3-dichloroacetone (3.7 g, 29 mmol). The resultant mixture was heated at reflux for 5 hours. The reaction mixture was then cooled and concentrated under reduced pressure. The residual oil was taken up in water (100 ml) and the aqueous mixture extracted with ethyl acetate (100 ml). The organic extract was dried (MgSO$_4$) and evaporated under reduced pressure. The crude product (a brown oil) was purified by trituration with chloroform (40 ml). The title compound a yellow solid was collected by filtration and air-dried (7.5 g, 74%). $^1$H NMR (CDCl$_3$) δ=3.02 (s, 1H), 3.06 (s, 1H), 4.72 (s, 2H), 7.24 (d, J=4 Hz, 1H), 7.72 (d, J=2 Hz, 1H), 7.78 (d, J=4 Hz, 1H), 8.72 (bs, 1H). Low Resolution Mass Spectroscopy: 347 (M+, 15).

EXAMPLE 12

2-[3-(N,N-Dimethylaminoethyl)indol-5-yl]-4-(chloromethyl)thiazole-borane complex To a suspension of the compound of Example 11 (3 g, 8.63 mmol) in dry tetrahydrofuran (75 ml) in an atmosphere nitrogen was added dropwise 1M borane in tetrahydrofuran (34.5 ml, 34.5 mmol, 4 eq). The reaction mixture was stirred at room temperature for 18 hours. A yellow solution was quenched carefully with aqueous sodium bicarbonate (10 ml) and concentrated under reduced pressure. The residual oil was partitioned between chloroform (75 ml) and water (75 ml). The organic extract was dried (MgSO$_4$) and evaporated under reduced pressure. Purification by flash chromatography of the crude product using silica gel (60 g), and elution with chloroform-methanol (20:1) yielded the title compound (1.72 g, 60%) as a yellow solid. $^1$H NMR (CDCl$_3$) δ=2.66 (s, 6H), 3.02 (m, 2H), 3.16 (m, 2H), 4.76 (s, 2H), 7.00 (bs, 1H), 7.34 (d, J=2 Hz, 1H), 7.74 (d, J=4 Hz, 1H), 8.16 (s, 1H), 8.82 (bs, 1H).

EXAMPLE 13

2-[3-(N,N-Dimethylaminoethyl)-indol-5-yl]-4-(phenylaminomethyl)thiazole

To a suspension of the compound of Example 12 (0.2 g, 0.6 mmol) in isopropyl alcohol (20 ml) was added sodium carbonate (0.1 g, 1 mmol) followed by an addition of aniline (0.065 ml, 0.7 mmol). The resultant mixture was heated at 60° C. for 3 hours. The reaction mixture was evaporated under reduced pressure. The residual solid was partitioned between chloroform (30 ml) and brine (30 ml). The organic extract was dried (MgSO$_4$) and evaporated under reduced pressure. Purification by flash chromatography of the crude product using silica gel (5 g) and elution with chloroform-methanol (5:1) yielded the title compound (0.1 g, 46%) as a yellow solid. $^1$H NMR (CDCl$_3$) δ=2.34 (s, 6H), 2.64 (t, J=3 Hz, 2H), 2.98 (t, J=3 Hz, 2H), 4.38 (bs, 1H), 4.50 (s, 2H), 6.65 (m, 3H), 7.02 (bs, 2H), 7.18 (t, J=3 Hz, 2H), 7.30 (d, J=4 Hz, 1H), 7.74 (d, J=3 Hz, 1H), 8.16 (bs, 1H), 8.30 (bs, 1H). Low Resolution Mass Spectroscopy: 376 (M+, 52). High Resolution Mass Spectroscopy: Calcd. for C$_{22}$H$_{24}$N$_4$S: 376.1689; Found: 376.1677.

EXAMPLE 14

General Procedures for the synthesis of 2-[3-(N,N-Dimethylaminoethyl)indol-5-yl]-4-substituted thiazoles To a suspension of the compound of Example 12 (0.2 g, 0.6 mmol) in isopropyl alcohol was added sodium carbonate (0.1 g, 1 mmol) followed by an addition of an appropriate aryl reagent (0.7 mmol). The resultant mixture was heated at 60° C. for 3 hours. The reaction mixture was evaporated under reduced pressure. The residual oil was partitioned between chloroform (30 ml) and brine (30 ml). The organic extract was dried (MgSO$_4$) and evaporated under reduced pressure. Purification by flash chromatography of the crude product using silica gel (5 g) and elution with chloroform-methanol (5:1) yielded the final compound.

14A. 2-[3-(N,N-Dimethylaminoethyl)indol-5-yl]-4-(2-methoxyphenylaminomethyl)thiazole The appropriate aromatic reagent was o-anisidine (86 mg, 0.7 mmol). Purification by flash chromatography of the crude product afforded 50 mg (20% yield) of the title compound as a white solid. $^1$H NMR (CDGl$_3$) δ-2.46 (s, 6H), 2.89 (t, J=4 Hz, 2H), 3.04 (t, J=4 Hz, 2H), 3.85 (s, 3H), 4.54 (s, 2H), 6.62–6.68 (m, 2H), 6.72–6.83 (.m, 2H), 7.01–7.05 (m, 2H), 7.31 (d, J=6 Hz, 1H), 7.72 (d, J=6 Hz, 1H), 8.14 (s, 1H), 8.48 (bs, 1H). Low Resolution Mass Spectroscopy: 406 (M+, 10).

14B. 2-[3-(N,N-Dimethylaminoethyl)indol-5-yl]-4-(3-methoxyphenylaminomethyl)thiazole The appropriate aromatic reagent was m-anisidine (86 mg, 0.7 mmol). Purification by flash chromatography of the crude product afforded 50 mg (20% yield) of the title compound as a colorless resin. $^1$H NMR (CDCl$_3$) δ=2.34 (s, 6H), 2.66 (t, J=4 Hz, 2H), 2.96 (t, J=4 Hz, 2H), 3.78 (s, 3H), 4.46 (s, 2H), 7.00–7.06 (m, 2H), 7.28 (d, J=6 Hz, 1H), 7.44–7.50 (m, 2H), 7.62–7.68 (m, 2H), 7.72 (d, J=6 Hz, 1H), 8.14 (s, 1H), 8.24 (bs, 1H). Low Resolution Mass Spectroscopy: 406 (M+, 10 ).

14C. 2-[3-(N,N-Dimethylaminoethyl]indol-5-yl]-4-(4-methoxyphenylaminomethyl]thiazole The appropriate aromatic reagent was p-anisidine (86 mg. 0.7 mmol). Purification by flash chromatography of the crude title compound afforded 60 mg of a yellow solid (25% yield). $^1$H NMR (CDCl$_3$) δ=2.40 (s, 6H), 2.72 (t, J=6 Hz, 2H), 3.01 (t, J=6 Hz, 2H), 3.74 (s, 3H), 4.26 (s, 2H), 6.66 (d, J=6 Hz, 2H), 6.76 (d, J=6 Hz, 2H) 7.02 (bs, 2H), 7.30 (d, J=4 Hz, 1H), 7.72 (d, J=4 Hz, 1H), 8.16 (s, 1H), 8.50 (bs, 1H). Low Resolution Mass Spectroscopy: 406 (M+, 10).

14D. 2-[3-(N,N-Dimethylaminoethyl)indol-5-yl]-4-(2-methylphenylaminomethyl]thiazole The appropriate aromatic reagent was o-toluidine (75 mg, 0.7 mmol). Purification by flash chromatography of the crude product afforded 40 mg (17% yield) of a white hygroscopic solid. $^1$H NMR (CDCl$_3$) δ=2.44 (s, 6H), 2.78 (t, J=4 Hz, 2H), 3.04 (t, J=4 Hz, 2H) , 4.52 (s, 2H) , 6.60–6.66 (m, 2H), 7.00–7.08 (m, 4H), 7.30 (d, J=6 Hz, 1H), 7.72 (d, J=6 Hz, 1H), 8.14 (s, 1H), 8.28 (bs, 1H). Low Resolution Mass Spectroscopy: 390 (M+, 10).

14E. 2-[3-(N,N-Dimethylaminoethyl)indol-5-yl]-4-(2-chlorophenylaminomethyl)thiazole The appropriate aromatic reagent was o-chloroaniline (89 mg, 0.7 mmol). Purification by flash chromatography of the crude product afforded 30 mg (12% yield) of the title compound as a colorless resin. $^1$H NMR (CDCl$_3$) δ=2.40 (s, 6H), 2.74 (t, J=4 Hz, 2H), 2.98 (t, J=4Hz, 2H), 4.54 (s, 2H), 6.50–6.68 (m, 2H), 6.98–7.08 (m, 3H), 7.20 (d, J=4 Hz, 1H), 7.32 (d, J=6 Hz, 1H), 7.70 (d, J=6 Hz, 1H), 8.12 (s, 1H), 8.68 (bs, 1H). Low Resolution Mass Spectroscopy: 410.2 (M+, 10)

14F. 2-[3-(N,N-Dimethylaminoethyl)indol-5-yl]-4-(N-methylphenylaminomethyl]thiazole The appropriate aromatic reagent was N-methylaniline (75 mg, 0.7 mmol). Purification by flash chromatography of a crude product afforded 50 mg (21% yield) of the title compound as a white solid. $^1$H NMR (CDCl$_3$) δ=2.70 (s, 6H), 3.08 (s, 3H), 3.10 (m, 2H), 3.22 (m, 2H), 4.68 (s, 2H), 6.64–6.82 (m, 4H), 7.06 (s, 1M), 7.18 (d, J=4 Hz, 1H), 7.38 (d, J=4 Hz, 1H), 7.66 (d, J=4 Hz, 1H), 8.08 (s, 1H), 9.14 (bs, 1H). Low Resolution Mass Spectroscopy: 390 (M+, 40).

14G. 2-[3-(N,N-Dimethylaminoethyl)indole 5-yl]-4-(benzylaminomethyl)thiazole

The appropriate aromatic reagent was benzylamine (75 mg, 0.7 mmol). Purification by flash chromatography of a crude product afforded 0.1 g (47% yield) of the title compound as a colorless resin. $^1$H NMR (CDCl$_3$) δ=2.34 (s, 6H,), 2.66 (t, J=4 Hz, 2H), 2.96 (t, J=4 Hz, 2H), 3.88 (s, 2H), 3.97 (s, 2H), 7.00 (bs, 2H), 7.20–7.36 (m, 6H), 7.71 (d, J=4 Hz, 1H), 8.16 (bs, 1H), 8.50 (bs, 1H). Low Resolution Mass Spectroscopy: 390 (M+, 10).

EXAMPLE 15

General Procedure for the Synthesis of 2-[3-(N,N-Dimethylaminoethyl)indol-4-yl]-4-phenoxy(-thiophenoxy)methylthiazoles To a solution of an appropriate aromatic alcohol (1 mmol) in dry tetrahydrofuran (10 ml) was added sodium hydride (57 mg, 1.2 mmol). The resultant mixture was stirred at room temperature under nitrogen atmosphere for 30 min. To a suspension of the compound of Example 12 (0.33 g, 1 mmol) in isopropyl alcohol (10 ml) was added a sodium salt of an appropriate alcohol in THF. The resultant mixture was heated at ~50° C. for 2 hrs. The reaction mixture was evaporated under reduced pressure. The residual oil was partitioned between chloroform (40 ml) and brine (40 ml). The organic extract was dried (MgSO$_4$) and evaporated under reduced pressure. Purification by flash chromatography of the crude product using silica gel (10 g) and elution with chloroform-methanol (5:1) yielded a final compound.

15A. 2-[3-(N,N-Dimethylaminoethyl)indol-5-yl]-4-(phenoxymethyl)thiazole

The appropriate aromatic alcohol was phenol (94 mg, 1 mmol). Purification by flash chromatography of the crude product afforded 50 mg (13% yield) of the title compound as a white solid. $^1$H NMR (CDCl$_3$) δ=2.36 (s, 6H), 2.64 (t, J=4 Hz, 2H), 2.96 (t, J=4 Hz, 2H), 5.26

(s, 2H), 6.90–7.01 (m, 4H), 7.20–7.32 (m, 4H), 7.74 (d, J=6 Hz, 1H), 8.16 (s, 1H), 8.24 (bs, 1H). Low Resolution Mass Spectroscopy: 377 (M+, 20).

15B. 2-[3-(N,N-Dimethylaminoethyl)indol-5-yl)-4-(thiophenoxymethyl)thiazole

The appropriate aromatic alcohol was thiophenol (0.11 g, 1 mmol). Purification by flash chromatography of the crude product afforded 0.11 g (28% yield) of the title compound as a colorless resin. $^1$H NMR (CDCl$_3$) δ=2.36 (s, 6H), 2.69 (t, J=6 Hz, 2H), 2.98 (t, J=6 Hz, 2H), 4.30 (s, 2H), 6.94 (s, 1H), 7.00 (s, 1H), 7.15 (d, J=6 Hz, 1H), 7.22–7.37 (m, 5H), 7.70 (d, J=6 Hz, 1H), 8.16 (S, 1H), 8.46 (bs, 1H). Low Resolution Mass Spectroscopy: 393 (M+, 55).

EXAMPLE 16

4-(1-Acetylindolin-5-yl)-2-methylthiazole

A mixture of the compound of preparation 5 (0.48 g, 2 mmol) and thioacetamide (0.23 g, 3 mmol) in ethanol (10 ml) was heated at reflux temperature. The reaction mixture was concentrated under reduced pressure. The residual light brown solid was dissolved in chloroform (20 ml), washed with water, dried (MgSO$_4$) and evaporated under reduced pressure to afford the title compound as a tan solid (0.41 g, 80% yield). $^1$H NMR (CDCl$_3$) δ=2.21 (s, 3H), 2.79 (s, 3H), 3.20 (t, J=6 Hz, 2H), 4.04 (t, J=6 Hz, 2H), 7.18 (s, 1H), 7.62 (d, J=4 Hz), 7.70 (s, 1H), 8.18 (d, J=4 Hz, 1H). Low resolution mass spectroscopy: 258 (M+, 50).

EXAMPLE 17

4-(Indolin-5-yl)-2-methylthiazole

The compound of Example 16 (0.41 g, 1.6 mmol) was heated at approximately 50° C. in 6N HCl (10 ml) for 1 hour. The resultant mixture was allowed to cool down to room temperature, then basified with solid sodium carbonate to a pH of 10. The aqueous mixture was extracted with CHCl$_3$ (3×10 ml). The combined chloroform extracts were washed with H$_2$O (20 ml), dried (MgSO$_4$), and evaporated under reduced pressure to afford 0.33 g (95% yield) of the title compound as a white solid. $^1$H NMR (CDCl$_3$) δ=2.72 (s, 3H), 3.00 (t, J=4 Hz, 2H), 3.52 (t, J=4 Hz, 2H), 6.58 (d, J=6 Hz, 1H), 7.00 (s, 1H), 7.50 (d, J=6 Hz, 1H), 7.60 (bs, 1H).

EXAMPLE 18

4-(Indol-5-yl)-2-methylthiazole

To a stirred mixture of the compound of Example 17 (0.33 g, 1.5 mmol) in xylenes (10 ml) was added chloranil (9.5 g, 2 mmol). The resultant mixture was heated at reflux for 1 hour. A brown mixture was allowed to cool down to room temperature and then was combined with 10 ml of 2N NaOH. This mixture was filtered through celite. The xylenes layer was separated, washed with 2N NaOH (10 ml), H$_2$O (10 ml), 0.5N HCl (10 ml) and H$_2$O (10 ml). The xylenes extract was dried (MgSO$_4$) and evaporated under reduced pressure. Purification by flash chromatography of the crude product using silica gel (15 g) and elution with ethyl acetate-hexane (1:1) yielded the title compound (0.2 g, 61%) as a brown solid. $^1$H NMR (CDCl$_3$) δ=2.44 (s, 3H), 7.08 (s, 1H), 7.12 (bs, 2H), 7.24 (bs, 1H) 7.28 (s, 1H), 7.32 (d, J=6 Hz, 1H).

EXAMPLE 19

4-[3-(1-tert-Butoxycarbonyl-1,2,5,6-tetrahydropyrid-4-yl)indol-4-yl]-2-methylthiazole A methanolic solution of sodium methoxide was prepared by the addition of sodium (26 mg, 1.1 mmol) to methanol (10 ml) under nitrogen at room temperature. This solution was mixed with a solution of the compound of Example 18 (0.12 g, 0.58 mmol) in methanol (10 ml) and stirred at room temperature for 30 minutes. A solution of N-t-butoxycarbonyl-4-piperidone (0.22 g, 1.12 mmol, 2 eq) in methanol (5 ml) was added to the reaction mixture. The resultant mixture was heated at reflux for 8 hours, cooled and then concentrated under reduced pressure. The residual oil was taken up in chloroform (20 ml), washed with H$_2$O (20 ml), dried (MgSO4) and evaporated under reduced pressure. Purification by flash chromatography of the crude product using silica gel (6 g) and elution with ethyl acetate-hexane 1:1 yielded the title compound (0.16 g, 72%) as a beige solid. $^1$H NMR (CDCl$_3$) δ=2.50 (s, 9H), 2.54 (bs, 2H), 2.80 (s, 3H), 3.66 (t, J=4 Hz, 2H), 4.12 (bs, 2H), 6.20 (bs, 1H), 7.19 (d, J=2 Hz, 1H), 7.25 (s, 1H), 7.36 (d, J=6 Hz, 1H), 7.68 (dd, J$_1$=2 Hz, J$_2$=6 Hz, 1H), 8.36 (s, 1H), 8.46 (bs, 1H).

EXAMPLE 20

4-[3-(1,2,5,6-Tetrahydropyrid-4-yl)indol-5-yl]-2-methylthiazole

To a stirred solution of the compound of Example 19 (0.14 g, 0.35 mmol) in methanol (5 ml) was added 5 ml of methanol saturated with gaseous hydrogen chloride. The resultant mixture was stirred at room temperature for 2 hours. The mixture was concentrated under reduced pressure. A crude product was triturated with methanol (3 ml). A light yellow solid was collected by filtration and air-dried to yield the title compound as a hydrogen chloride salt (70 mg, 60%). $^1$H NMR (CDCl$_3$) δ=2.74 (bs, 5H), 3.32 (bs, 2H), 3.80 (bs, 2H), 6.21 (bs, 1H), 7.42 (d, J=6 Hz, 1H), 7.64 (d, J=2 Hz, 1H), 7.72 (dd, J=2 Hz, J$_2$=6 Hz, 1H), 7.80 (s, 1H), 8.38 (s, 1H), 9.10 (bs, 1H). Low resolution mass spectroscopy: 295 (M+, 100).

EXAMPLE 21

General Procedures for the Synthesis of 4-substituted 2-[3-(N,N-dimethylaminoethyl)indol-5-yl]thiazoles To a stirred solution of the compound of Example 10 (0.28 g, 1 mmol) in ethanol (15 ml) was added an appropriate aromatic α-chloroketone (1 mmol). The resultant mixture was heated at reflux temperature for 2–4 hours. Product precipitated out of the reaction mixture upon cooling to room temperature, the solid material was collected by filtration, washed with a small amount of ethanol (3 ml) and air-dried to afford an appropriate intermediate.

21A. 2-[3-(N,N-Dimethylglyoxamid)indol-5-yl-4-phenylthiazole

The appropriate aromatic α-chloroketone was 2-chloroacetophenone (0.16 g, 1 mmol). Reflux time was 2 hours. The title compound was isolated as a tan solid (0.31 g, 58% ). $^1$H NMR (CDCl$_3$) δ=3.02 (s, 3H), 3.06 ( s, 3H), 6.94 (bs, 1H), 7.23–7.44 (m, 5H), 7.81 (d, J=6 Hz, 1H), 8.00 (d, J=6 Hz, 2H), 8.24 (s, 1H), 8.68 (bs, 1H).

21B. 2-[3-(N,N-Dimethylglyoxamid)indol-5-yl]-4-benzylthiazole

The appropriate aromatic e-chloroketone was 1-chloro-3-phenyl-2-propanone (0.17 g, 1 mmol). Reflux time was 2 hours. The title compound was isolated as a white solid $^1$H NMR (CDCl$_3$) $\delta=3.00$ (s, 3H), 3.04 (s, 3H), 4.32 (s, 2H), 6.74 (s, 1H), 7.24–7.36 (m, 5H), 7.26 (d, J=6 Hz, 2H), 7.96 (bs, 1H), 8.03 (d, J=6 Hz, 1H), 8.72 (s, 1H).

21C. 2-[3-(N,N-Dimethylglyoxamid)indol-5-yl]-4-phenethylthiazole

The appropriate aromatic e-chloroketone was 1-chloro-4-phenyl-2-butanone (0.18 g, 1 mmol). Reflux time was 4 hours. The title compound was isolated as a beige solid (0.30 g, 75%). $^1$H NMR (CDCl$_3$) $\delta=3.00$ (s, 9H), 3.06 (s, 3H), 3.20 (t, J=4 Hz, 2H), 3.44 (t, J=4 Hz, 2H), 6.86 (s, 1H), 7.18–7.26 (m, 6H), 7.66 (d, J=6 Hz, 1H), 7.98 (s, 1H), 8.26, (d, J=6 Hz, 1H), 8.72 (bs, 1H).

EXAMPLE 22

General Procedure for the Reduction of 2-[3-(N,N-Dimethylglyoxamid)indol-5-yl]-4-substituted thiazole To a solution of the desired compound from Example 21 in dry tetrahydrofuran (10 ml) in an atmosphere of nitrogen was added dropwise 1M borane in tetrahydrofuran (4 eq). The reaction mixture was stirred at room temperature for 18 hours.

A yellow solution was quenched carefully with aqueous sodium bicarbonate (5 ml) and concentrated under reduced pressure. The residual oil was partitioned between chloroform (20 ml) and water (20 ml). The organic extract was dried (MgSO$_4$) and evaporated under reduced pressure. Purification by flash chromatography of the crude product yielded the desired compound as a borane complex.

22A. 2-[3-(N,N-Dimethylaminoethyl)indol-5-yl]-4-phenylthiazole-borane complex The appropriate intermediate was the compound of Example 21A (0.2 g, 0.53 mmol) and 2.1 ml of 1M borane in tetrahydrofuran (2.1 mmol) was used. Purification by flash chromatography of the crude product using silica gel (5 g) and elution with chloroform-methanol (20:1) yielded the title compound (0.1 g, 54%) as a yellow solid. $^1$HNMR (CDCl$_3$ $\delta=2.68$ (s, 6H), 3.04–3.10 (m, 2H), 3.20–3.28(m, 2H), 7.04 (s, 1H), 7.30 (d, J=6 Hz, 1H), 7.34–7.44 (m, 4H), 7.86 (d, J=6 Hz, 1H), 7.98 (d, J=6 Hz, 2H), 8.12 (bs, 1H).

22B. 2-[3-(N,N-Dimethylaminoethyl)indol-5-yl]-4-benzylthiazole-borane complex The appropriate intermediate was the compound of Example 21B (0.21 g, 0.54 mmol) and 2.2 ml of 1M borane in tetrahydrofuran (2.2 mmol) was used. Purification by flash chromatography of the crude product using silica gel (5 g) and elution with chloroform-methanol (20:1) afforded the title compound (0.18 g, 95%) was a yellow solid. $^1$H NMR (CDCl$_3$) $\delta=2.68$ (s, 6H), 3.02–3.08 (m, 2H), 3.20–3.26 (m, 2H), 4.21 (bs, 2H), 6.62 (s, 1H), 7.02 (s, 1H), 7.24–7.32 (m, 6H), 7.36 (d, J=6 Hz, 1H), 7.74 (d, J=6 Hz, 1H), 8.14 (bs, 1H).

22C. 2-[3-(N,N-Dimethylaminoethyl)indol-5-yl)-4-phenethylthiazole-borane complex The appropriate intermediate was compound of Example 21C (0.27 g, 0.67 mmol) and 2.7 ml of 1M borane in tetrahydrofuran (2.7 mmol) was used. Purification by flash chromatography of the crude product using silica gel (6 g) and elution with chloroform-methanol (20:1) yielded the title compound (0.15 g, 58%) as a yellow solid. $^1$NMR (CDCl$_3$) $\delta=2.62$ (s, 6H), 3.00–3.06 (m, 2H), 3.18–3.21 (m, 2H), 6.68 (s, 1H), 6.92 (s, 1H), 7.10–7.22 (m, 5H), 7.28 (d, J=6 Hz, 1H), 7.70 (d, J=6 Hz, 1H), 8.10 (s, 1H), 8.48 (bs, 1H).

EXAMPLE 23

General Procedure for Removal of the Borane Complex

To a solution of one of the compounds from Example 22 in methanol (5 ml) were added solid sodium carbonate (3 eq) and cesium fluoride (0.4 eq). The resultant mixture was heated at reflux temperature for 24 hours. A white suspension was concentrated under reduced pressure. The residual solids were partitioned between ethyl acetate (5 ml) and water (5 ml). The organic extract was dried (MgSO$_4$) and evaporated under reduced pressure. Purification by flash chromatography of the crude product using silica gel (4 g) and elution with chloroform-methanol (5:1) yielded a final product.

23A. 2-[3-(N,N-Dimethylaminoethyl)indol-5-yl]-4-phenylthiazole

The appropriate intermediate was the compound of Example 22A (0.1 g, 0.28 mmol); 89 mg (0.84 mmol) of sodium carbonate and 18 mg (0.11 mmol) of cesium fluoride were used. Purification of the crude product by flash chromatography yielded the title compound (80 mg, 82%) as a yellow solid. $^1$H NMR (CDCl$_3$) $\delta=2.36$ (s, 6H), 2.68 (t, J=6 Hz, 2H), 2.99 (t, J=6 Hz, 2H), 6.94 (s, 1H), 7.22–7.42 (m, 5H), 7.81 (d, J=4 Hz, 1H), 8.00 (d, J=4 Hz, 2H), 8.24 (s, 1H), 8.68 (bs, 1H). Low Resolution Mass Spectroscopy: 347 (M+, 50).

23B. 2-[3-(N,N-Dimethylaminoethyl)indol-5-yl]-4-benzylthiazole

The appropriate intermediate was the compound of Example 22B (0.15 g, 0.4 mmol); 127 mg (1.2 mmol) of sodium carbonate and 24 mg (0.16 mmol) of cesium fluoride were used. Purification of the crude product by flash chromatography yielded the title compound (78 mg, 54%) as a colorless thick oil. $^1$H NMR (CDCl$_3$) $\delta=2.34$ (s, 6H), 2.58 (t, J=4 Hz, 2H), 2.88 (t, J=4 Hz, 2H), 4.14 (s, 2H), 6.56 (s, 1H), 6.86 (s, 1H), 7.14–7.17 (m, 3H), 7.20–7.28 (m, 3H), 7.64 (d, J=6 Hz, 1H), 8.08 (s, 1H), 8.70 (bs, 1H). High Resolution Mass Spectroscopy: calculated for C$_{22}$H$_{23}$N$_3$S$_1$: 361.1612; found 361.1624. Low Resolution Mass Spectroscopy: 361 (M+, 100).

23C. 2-[3-(N,N-Dimethylaminoethyl)indol-4-yl]-4-phenethylthiazole

The appropriate intermediate was the compound of Example 22C (0.15 g, 0.39 mmol); 0.12 g (1.17 mmol) of sodium carbonate and 24 mg (0.16 mmol) of cesium fluoride were used. Purification of the crude product by flash chromatography afforded the title compound (50 mg, 34%) as a yellow solid. $^1$H NMR (CDCl$_3$) $\delta=2.38$ (s, 6H), 2.68 (t, J=4 Hz, 2H), 2.98 (t, J=4 Hz, 2H), 3.12 (bs, 4H), 6.64 (s, 1H), 7.00 (s, 1H), 7.14–7.30 (m, 6H), 7.74 (d, J=6 Hz, 1H), 8.17 (s, 1H), 8.40 (bs, 1H). Low Resolution Mass Spectroscopy: 375 (M+, 100). High Resolution Mass Spectroscopy, calculated for C$_{23}$H$_{25}$N$_3$S$_1$: 375. 1753; found: 375.1765.

EXAMPLE 24

2-(1-Phenylsulfonylindol-5-ylmethyl-4-methylthiazole

Procedure as described in Example 3. The reagents included the compound of Preparation 10 (0.25 g, 0.75 mmol), chloroacetone (0.08 ml, 1 mmol) and ethanol (5 ml). Purification by flash chromatography of the crude product (0.35 g) using silica gel (10 g) and elution with hexane-ethyl acetate (50:50) yielded 0.15 g (54%) of the title compound as a beige solid. $^1$H NMR (CDCl$_3$) d=2.40 (s, 3H), 4.32 (s, 2H), 6.58 (d, J=2 Hz, 1H), 6.68 (s, 1H), 7.22 (d, J=4 Hz, 1H), 7.34–7.40 (m, 4H), 7.46–7.50 (m, 2H), 7.82 (d, J=4 Hz, 1H), 7.88 (d, J=6 Hz, 1H).

EXAMPLE 25

2-[3-(1-tert-Butoxycarbonyl-1,2,5,6-tetrahydropyrid-4-yl)indol-5-ylmethyl]-4-methylthiazole Procedure identical as in Example 4. The reagents included the compound of Example 24 (0.13 g, 0.35 mmol), N-tert-butoxycarbonyl-4-piperidone (0.13 g, 0.65 mmol), sodium (48 mg, 1 mmol) and methanol (10 ml). Purification by flash chromatography of the crude product (0.11 g) using silica gel (3 g) and elution with chloroform afforded 70 mg (51%) of the title compound as a light brown solid. $^1$H NMR (CDCl$_4$) δ=2.02 (S, 9H), 2.39 (s, 3H), 2.42–2.48 (m, 2H), 3.62 (t, J=2 Hz, 2H), 4.04–4.09 (m, 2H), 4.36 (s, 2H), 6.08 (bs, 1H), 6.64 (s, 1H), 7.08–7.11 (m, 2H), 7.23 (d, J=6 Hz, 1H), 7.74 (s, 1H), 8.88 (bs, 1H).

EXAMPLE 26

2-[3-(1,2,5,6-Tetrahydropyrid-4-yl)indol-5-ylmethyl]-4-methylthiazole

Procedure as described in Example 8. The reagents included the compound of Example 25 (70 mg. 0.18 mmol), methanol (2 ml) and methanolic HCl (2 ml). Purification by flash chromatography using-silica gel (3 g) and elution with triethylamine methanol (5:95) afforded a final compound (50 mg, 90%) as a yellow solid. $^1$H NMR (CDCl$_3$) δ=2.40 (s, 3H), 2.43–2.50 (m, 2H), 3.13 (t, J=4 Hz, 2H), 3.55–3.60 (m, 2H), 4.40 (s, 2H), 6.22 (bs, 1H), 6.68 (s, 1H), 7.12–7.16 (m, 2H), 7.30 (d, J=6 Hz, 1H), 7.71 (s, 1H), 8.52 (bs, 1H). Low Resolution Mass Spectroscopy: 309 (M+, 100).

EXAMPLE 27

2-[3-(1-Methylpiperidin-4-yl]indol-5-yl]-4-(chloromethyl)thiazole

Procedure identical to Example 11. The reagents used include the compound of Preparation 13 ( 0.4 g, 1.4 mmol), 1,3-dichloroacetone (0.18 g, 1.4 mmol) and isopropanol (15 ml). Reflux time was 2 hours. A crude product (a brown foam) was purified by trituration with chloroform (5 ml). The title compound was collected by filtration and air-dried (0.42 g, 87%). $^1$H NMR (CDCl$_3$) δ=1.60–1.70 (m, 2H), 1.74–1.82 (m, 2H), 2.10 (dd, J=2 Hz, J$_2$m 6 Hz, 2H), 2.34 (s, 3H), 2.74–2.86 (m, 1H), 2.98 (d, J=6 Hz, 2H), 4.72 (s, 2H), 6.98 (s, 1H), 7.28 (d, J m 6 Hz, 1H), 7.34 (s, 1H), 7.66 (d, J=6 Hz, 1H), 8.10 (s, 1H), 8.20 (bs, 1H).

EXAMPLE 28

2-[3-(1-Methylpiperidin-4-yl)indol-5-yl]-4-(phenylaminomethyl)thiazole

Procedure identical to Example 14. The reagents used include the compound of Example 27 (0.19 g, 0.44 mmol), aniline (0.05 ml, 0.55 mmol), sodium carbonate (0.11 g, 1 mmol) and isopropanol (5 ml). Reflux time was 1 hour. Purification by flash chromatography of the crude product using silica gel (4 g) and elution with chloroform-methanol (5:1) yielded the title compound (40 mg, 25%) as a brown solid. $^1$H NMR (CDCl$_3$) δ=2.04–2.24 (m, 4H), 2.60–2.74 (m, 2H), 2.66 (s, 3H), 2.94–3.04 (m, 1H), 3.36 (d, J=6 Hz, 2H), 4.46 (s, 2H), 6.42–6.50 (m, 3H), 6.98 (bs, 1H), 7.00 (s, 1H), 7.14 (t, J=6 Hz, 2H), 7.38 (d, J=6 Hz, 1H), 7.66 (d, J=6 Hz, 1H), 8.12 (s, 1H), 8.88 (bs, 1H). Low Resolution Mass Spectrum: 402 (M+, 40).

EXAMPLE 29

4-(1-Acetylindolin-5-yl)-2-benzylthiazole

The procedure as described in Example 16 was used. The compound of Preparation 5(3.14 g, 13.24 mmol) was reacted with benzyl thiocarboxamide (2 g., 13.24 mmol) in boiling ethanol (75 ml) for 6 hours. The title compound was isolated as a beige solid (3.1 g, 70%). $^1$H NMR (CDCl$_3$) δ=2.13 (s, 6H), 3.19 (t, J=6 Hz, 2H), 4.03 (t, J=6 Hz, 2H), 4.35 (s, 2H), 7.22–7.35 (m, 6H), 7.65 (d, J=6 Hz, 1H), 7.73 (s, 1H), 8.20 (d, J=6 Hz, 1H).

EXAMPLE 30

4-(Indol-5-yl)-2-benzylthiazole

The procedure as described in Example 17 was used. The title compound was isolated as a brown solid (2.2 g, 84%). $^1$H NMR (CDCl$_3$) δ=3.22 (t, J=6 Hz, 2H), 4.08 (t, J=6 Hz, 2H), 4.34 (s, 5H), 7.28–7.41 (m, 6H), 7.64 (d, J=6 Hz, 1H), 7.75 (s, 1H), 8.22 (d, J=6 Hz, 1H).

EXAMPLE 31

4-(Indol-5-yl)-2-benzylthiazole

To a stirred solution of the compound of Example 30 (2 g, 6.84 mmol) in benzene (20 ml) was added 2,3-dichloro-5, 6-dicyano-1,4 benzoquinone (2 g. 8.8 mmol). The resultant mixture was stirred at room temperature for 2.5 hours. A brown suspension was evaporated under reduced pressure. Purification by flash chromatography of the crude product using silica gel (60 g) and elution with ethyl acetate yielded the title compound (1.2 g, 60.5%) as a yellow solid. $^1$H NMR (CDCl$_3$) δ=4.40 (s, 2H), 6.58 (bs, 1H), 7.17 (t, J=4 Hz, 1H), 7.24–7.39 (m, 7H), 7.72 (d, J=6 Hz, 1H), 8.21 (s, 1H), 8.37 (bs, 1H).

EXAMPLE 32

4-[3-(N,N-Dimethylglyoxamid)indol-5-yl]-2-benzylthiazole

The procedure as described in Example 9 was used. The compound of Example 31 (0.29 g, 1 mmol) was reacted with oxalyl chloride (0.15 ml, 1.7 mmol) and phthalimide (59 mg, 0.4 mmol) in dry diethyl ether (15 ml). Purification by flash chromatography of the crude product using silica gel (9 g) and elution with chloroform-methanol (20:1) yielded the title compound (0.25 g, 64%) as a tan-solid. $^1$H NMR (CDCl$_3$) δ=2.97 (s, 3H), 3.02 (s, 3H), 4.37 (s, 2H), 7.25–7.35 (m, 8H), 7.71 (bs, 1H), 7.78 (d, J=6 Hz, 1H), 8.74 (s, 1H).

EXAMPLE 33

4-[3-(N,N-Dimethylaminoethyl)indol-5-yl]-2-benzylthiazole

The procedure as described in Example 12 was used. The crude product was isolated as a borane complex (0.15 g, 71% yield). Conversion of the borane complex by the procedure as described in Example 23 gave the title compound (60 mg, as a yellow oil. $^1$H NMR (CDCl$_3$) δ=2.35 (s, 6H), 2.69 (t, J=6 Hz, 2H), 2.98 (t, J=6 Hz, 2H), 4.40 (s, 2H), 7.00 (s, 1H), 7.24–7.36 (m, 7H), 7.68 (d, J=6 Hz, 1H), 8.14 (s, 1H), 8.18 (bs, 1H). High Resolution Mass Spectroscopy, calculated for $C_{22}H_{23}N_3S_1$: 361.5098; found: 361.1603.

EXAMPLE 34

2-[3(N,N-Dimethylalyoxamid)indol-5-yl]-4-arylthiazoles

Identical procedure as described in Example 21.

34A. 2-[3-(N,N-Dimethylglyoxamid)indol-5-yl]-4-(2-fluorobenzyl)thiazole

The compound of Example 10 (0.43 g, 1.6 mmol) was refluxed with 1-chloro-3-(2-fluorophenyl)-2-propanone (0.3 g, 1.6 mmol) in isopropanol for 5 hours. The title compound was isolated as a beige solid (0.4 g, 66% ). $^1$H NMR (CDCl$_3$) δ=3.02 (s, 3H), 3.06 (s, 3H), 4.18 (s, 2H), 6.70 (s, 1H), 6.96–7.06 (m, 2H), 7.12–7.28 (m, 3H), 7.34 (d, J=6 Hz, 1H), 7.86 (s, 1H), 7.88 (dd, J$_1$=6 Hz, J$_2$=2 Hz, 1H), 8.72 (bs, 1H).

34B. 2-[3-(N,N-Dimethylglyoxamid)indol-5-yl]-4-(2-nitrobenzyl)thiazole

The compound of Example 10 (0.77 g, 2.8 mmol) and 1-chloro-3-(2-nitrophenyl)-2-propanone (0.6 g, 2.8 mmol) were refluxed in isopropanol for 5 hours. The title compound was isolated as a tan solid (0.69 g, 61%). $^1$H NMR (CDCl$_3$) δ=3.03 (s, 3H), 3.07 (s, 3H), 4.52 (s, 2H), 6.88 (s, 1H), 7.26 (m, 5H), 7.80 (dd, J$_1$=6 Hz, J$_2$=2Hz, 1H), 7.83 (d, J=4 Hz, 1H), 7.96 (d, J=6 Hz, 1H), 8.84 (bs, 1H).

34C. 2-[3-(N,N-Dimethylglyoxamid)indol-5-yl]-4-(4-methoxybenzyl)thiazole

The compound of Example 10 (0.28 g, 1 mmol) and 1-chloro-3-(4-methoxybenzyl)-2-propanone (0.2 g, 1 mmol) were refluxed in ethanol for 8 hours. The title compound was isolated as a yellow solid (0.25 g, 64% ). 1H NMR (CDCl$_3$) δ=3.01 (s, 3H), 3.06 (s, 3H), 3.78 (s, 3H), 4.12 (s, 2H), 6.78–6.90 (m, 3H), 7.14–7.30 (m, 4H), 7.76 (d, J=3 Hz, 1H), 7.80 (d, J=6 Hz, 1H), 8.75 (bs, 1H).

34D. 2-[3-(N,N-Dimethylglyoxamid)indol-5-yl]-4-(3-pyridyl)thiazole

The compound of Example 10 (1.02 g, 3.73 mmol) and 1-bromo-2(3-pyridyl)-2-ethanone(1.1 g, 3.73 mmol) were refluxed in ethanol for 3 hours. The title compound was isolated as a yellow solid (0.9 g, 64%). $^1$H NMR (DMSO) δ=2.95 (s, 3H), 3.01 (s, 3H), 7.50 (dd, J$_1$=6Hz, J$_2$=1 Hz, 1H), 7.63 (d, J=6 Hz, 1H), 7.98 (d, J=6 Hz, 1H), 8.20 (s, 1H), 8.28 (s, 1H), 8.36 (d, J=6 Hz, 1H), 8.51 (d, J=1 Hz, 1H), 8.71 (s, 1H), 9,21 (bs, 1H).

EXAMPLE 35

2-[3-(N N-Dimethylaminoethyl)indol-5-yl]-4-arythiazoles

The procedure as described in Examples 22 and 23 was used.

35A. 2-[3-(N,N-Dimethylaminoethyl)indol-5-yl]-4-(2-fluorobenzyl)thiazole

The compound of Example 34A (0.38 g, 1 mmol) was reduced with 1M borane THF (4 ml, 4 mmol) using the procedure as described in Example 22. The crude product was isolated as a borane complex (0.35 g, 96%). Conversion of the borane complex by the procedure described in Example 23 gave the title compound (0.2 g, 69%). $^1$H NMR (CDCl$_3$) δ=2.52 (s, 6H), 2.89 (t, J=5 Hz, 2H), 3.12 (t, J=5 Hz, 2H), 4.21 (s, 2H), 6.69 (s, 1H), 7.05–7.11 (m, 3H), 7.24–7.31 (m, 2H), 7.60 (d, J=8 Hz, 1H), 7.74 (dd, J$_1$=7 Hz, J$_2$=3Hz, 1H), 8.14 (s, 1H), 8.39 (bs, 1H). High Resolution Mass Spectroscopy, calculated $C_{22}H_{22}N_3F_1S_1$: 379.5009; found: 3/9.1498.

35B. 2-[3-(N,N-Dimethylaminoethyl)indol-5-yl]-4-(2-nitrobenzyl)thiazole

The compound of Example 34B (0.67 g, 1.65 mmol) was reduced with 1M borane THF (7 ml, 7 mmol) using the procedure as described in Example 22. The crude product was isolated as a borane complex (0.64 g, 99%). Conversion of the borane complex by the procedure described in Example 23 afforded the title compound (0.2 g, 52%) as a light yellow solid. $^1$H NMR (CDCl$_3$) δ=2.35 (s, 6H), 2.66 (t, J=6 Hz, 2H), 2.97 (t, J=6 Hz, 2H), 6.81 (s, 1H), 7.04 (d, J=3 Hz, 1H), 7.31–7.42 (m, 2H) 7.46–7.51 (m, 2H), 7.73 (dd, J$_1$=6 Hz, J$_2$=3Hz, 1H), 7.94 (d, J=6 Hz, 1H), 8.05 (bs, 1H), 8.15 (s, 1H). High Resolution Mass Spectrometry, calculated for $C_{22}H_{22}N_4O_2S_1$: 406.50841 found: 406.1384.

35C. 2-[3-(N,N-Dimethylaminoethyl)indol-5-yl]-4-(4-methoxybenzyl)thiazole

The compound of Example 34C (0.21 g, 0.54 mmol) was reduced with 1M borane THF (3 ml, 3 mmol) using the procedure as described in Example 22. The crude product was isolated as a borane complex (0.18 g, 88%). Conversion of the borane complex by the procedure described in Example 23 gave the title compound (50 mg, 44%) as a colorless oil. $^1$H NMR (CDCl$_3$) δ=2.33 (s, 6H), 2.65 (t, J=7 Hz, 2H), 2.96 (t, J=7 Hz, 2H), 3.78 (s, 3H), 4.13 (s, 2H), 6.60 (s, 1H), 6.85 (dd, J$_1$=6Hz,J$_2$=2 Hz, 2H), 7.00 (s, 1H), 7.24–7.31 (m, 3H), 7.74 (dd, J$_1$=7 H$_z$, J$_2$=3 Hz, 1H), 8.16 (s, 1H), 8.41 (bs, 1H). High Resolution Mass Spectrometry, calculated for $C_{23}H_{25}N_3O_1S_1$: 391.1537; found 391.1717.

35D. 2-[3-(N,N-Dimethylaminoethyl)indol-5-yl]-4-(3-pyridyl)thiazole

The compound of Example 34D (0.8 g, 2.13 mmol) was reduced with 1M borane THF (6 ml, 6 mmol) using the procedure described in Example 22. The crude product was isolated as a borane complex (0.45 g, 58%). Conversion of the borane complex by the procedure described in Example 23 afforded the title compound (0.19 g, 66%) as a colorless oil. $^1$H NMR (CDCl$_3$) δ=2.37 (s, 6H), 2.71 (t, J=8 Hz, 2H), 3.01 (t, J=8 Hz, 2H), 7.06 (s, 1H), 7.34–7.40 (m, 2H), 7.48 (s, 1H), 7.85 (d, J=8 Hz, 1H), 8.25 (s, 1H), 8.31 (dd, J$_1$=8 Hz, J$_2$=3 Hz, 1H), 8.55 (m, 1H), 8.60 (bs, 1H), 9.22 (s, 1H). High Resolution Mass Spectrometry, calculated for $C_{20}H_{20}N_4S_1$: 348.4717; found 348.1398.

EXAMPLE 36

General Procedure for the Synthesis of 2-[3-N,N-Dimethylglyoxamid)indol-5-yl]-4[alkyl(aryl)amino]thiazoles The compound of Preparation 15 was transformed into its acid chloride using standard methodology (thionyl chloride, 50° C., 1 hour.). To a suspension of the acid chloride (0.3 g, 0.83 mmol) in methylene chloride (20 ml) was added an appropriate amino reagent. The resultant mixture was stirred at ambient temperature for 2 hours. A beige suspension was quenched with aq. NaHCO$_3$ (20 ml). An organic layer was separated, washed with H$_2$O (20 ml), dried (MgSO$_4$) and evaporated under reduced pressure. Purification by flash chromatography of the crude product using silica gel (15 g) and elution with chloroform-methanol (10:1) yielded the title compound.

36A. 2-[3-N,N-Dimethylglyoxamid)indol-5-yl]-4-(piperidinocarboxamid)thiazole

The appropriate amino reagent was piperidine (0.2 ml, 2 mmol). Purification of the crude product by flash chromatography afforded 0.29 g (85%) of the title compound as a yellow oil. $^1$H NMR (CDCl$_3$) $\delta = 1.52$–1.70 (m, 6H), 3.10 (s, 3H), 3.12 (s, 3H), 3.72–3.84 (m, 4H), 7.42 (d, J=8 Hz, 1H), 7.74 (s, 1H), 7.82 (d, J=8 Hz, 1H), 8.84 (s, 1H).

36B. 2-[3-N,N-Dimethylglyoxamid)indol-5-yl]-4-(cyclohexylocarboxamid)thiazole

The appropriate amino reagent was cyclohexylamine (0.23 ml, 2 mmol). Purification of the crude product by flash chromatography gave the title compound (0.28 g, 80%) as a yellow oil. $^1$H NMR (CDCl$_3$) $\delta = 1.28$–1.42 (m, 4H){}, 1.62–1.82 (m, 2H), 1.96–2.06 (m, 2H), 3.08 (s, 3H), 3.10 (m, 3H), 3.90–3.98 (m, 1H), 7.44 (d, J=8 Hz, 1H), 7.92–7.98 (m, 2H), 8.07 (s, 1H), 8.82 (s, 1H).

36C. 2-[3-N,N-Dimethylalyoxamid)indol-5-yl]-4-(4-tert-butylphenylcarboxamid)thiazole The appropriate amino reagent was 4-tert-butylaniline (0.15 g, 1.0 mmol). Purification by flash chromatography of the crude product yielded 0.19 g (49%) of the title compound as a tan solid. $^1$H NMR (CDCl$_3$) $\delta = 1.31$ (s, 9H), 3.09 (s, 3H), 3.11 (s, 3H), 7.36–7.39 (m, 2H), 7.44 (d, J=6 Hz, 1H), 7.64–7.67 (m, 2H), 7.91–7.96 (m, 2H), 8.13 (s, 1H), 8.87 (bs, 1H), 9.29 (bs, 1S), 9.98 (bs, 1H).

36D. 2-[3-N,N-Dimethylglyoxamid)indol-5-yl]-4-(2-trifluoromethylphenylcarboxamid)thiazole The appropriate amino reagent was 2-aminobenzotrifluoride (0.26 ml, 2.07 mmol). Purification of the crude product by flash chromatography afforded 0.35 g (90%) of the title compound as a beige solid. $^1$H NMR (CDCl$_3$) $\delta = 3.06$ (s, 3H), 3.09 (s, 3H), 7.16–7.25 (m, 2H), 7.37 (d, J=8 Hz, 1H), 7.56 (t, J=6 Hz, 1H), 7.62 (d, J=6 Hz, 1H), 7.74 (d, J=3 Hz, 1H), 7.92 (dd, J$_1$=8 Hz, 1H), 8.10 (s, 1H), 8.52 (d, J=8 Hz, 1H), 8.74 (bs, 1H).

EXAMPLE 37

General Procedure for the synthesis of 2-[3-N,N-Dimethylaminoethyl)indol-5-yl]-4-[alkyl](aryl) amino]thiazoles To a solution of an appropriate compound from Example 36 in dry tetrahydrofuran in an atmosphere of nitrogen was added dropwise 1M borane (6 eq.) in tetrahydrofuran. The resultant mixture was heated at about 50° C. for 8 hours. The reaction mixture was cooled to ambient temperature. A yellow solution was quenched carefully with aqueous sodium bicarbonate (5 ml) and concentrated under reduced pressure. The residual oil was partitioned between chloroform (25 ml) and water (25 ml). The organic extract was dried (MgSO$_4$) and evaporated under reduced pressure. Purification by flash chromatography of the crude product yielded the desired compound as a borane complex. Conversion of the borane complex by the procedure described in Example 23 afforded the title compound.

37A. 2-[3-N,N-Dimethylaminoethyl]indol-5-yl]-4-(N-piperidinomethyl]thiazole

The title compound was isolated as a colorless resin (45 mg, 53%). $^1$H NMR (CDCl$_3$) $\delta = 1.34$–1.46 (m, 2H), 1.54–1.66 (m, 4H), 2.33 (s, 6H), 2.44–2.58 (m, 4H), 2.62 (t, J=6 Hz, 2H), 2.92 (t, J=6 Hz, 2H), 4.71 (s, 2H), 6.95 (bs, 1H), 7.03 (s, 1H), 7.24 (d, J=6 Hz, 1H), 7.68 (dd, J$_1$=6 Hz, J$_2$=3 Hz, 1H), 8.13 (d, J=3 Hz, 1H), 8.98 (bs, 1H). Low Resolution Mass Spectroscopy: 368.2 (M+, 20).

37B. 2-[3-N,N-Dimethylaminoethyl]indol-5-yl]-4-(cyclohexylaminomethyl]thiazole

The title compound was isolated as a yellow resin (60 mg, 65%). $^1$H NMR (CDCl$_3$) $\delta = 1.10$–1.28 (m, 4H), 2.56–2.66 (m, 2H), 2.64–2.85 (m, 2H), 2.91–3.03 (m, 2H), 2.38 (s, 6H), 2.68 (t, J=6 Hz, 2H), 2.98 (t, J=6 Hz, 2H), 3.22–3.1 (m, 1H), 4.01 (s, 2H), 7.01 (s, 1H), 7.02 (d, J=6 Hz, 1H), 7.32 (d, J=6 Hz, 1H), 7.72 (d, J=6 Hz, 1H), 8.16 (s, 1H), 8.41 (bs, 1H). Low Resolution Mass Spectroscopy, calculated for C$_{22}$H$_{31}$N$_4$S$_1$: 383.5811; found: 383.2254.

37C. 2-[3-N,N-Dimethylaminoethyl)indol-5-yl]-4-(tert-butylphenylaminomethyl)thiazole The title compound was isolated as a yellow resin (0.11 g, 51%). $^1$H NMR (CDCl$_3$) $\delta = 1.29$ (s, 9H), 2.37 (s, 6H), 2.67 (t, J=6 Hz, 2H), 2.98 (t, J=6 Hz), 4.51 (s, 2H), 6.60–6.68 (m, 3H), 7.00–7.08 (m, 2H), 7.23 (d, J=7 Hz, 1H), 7.32 (d, J=6 Hz, 1H), 7.74 (d, J=6 Hz, 1H), 8.16 (bs, 1H), 8.39 (bs, 1H). High Resolution Mass Spectroscopy, calculated for C$_{26}$H$_{33}$N$_4$S$_1$: 433.6410; found: 433.2409.

37D. 2-[3-N,N-Dimethylaminoethyl)indol-5-yl]-4-(2-trifluoromethylphenylaminomethyl)thiazole The title compound was isolated as a colorless resin (70 mg, 48%). $^1$H NMR (CDCl$_3$) $\delta = 2.41$ (s, 6H), 2.72 (t, J=6 Hz, 2H), 3.01 (t, J=6 Hz, 2H), 4.60 (d, J=3 Hz, 2H), 5.17–5.24 (m, 1H), 6.70–6.78 (m, 2H), 6.98–7.04 (m, 2H), 7.29–7.36 (m, 2H), 7.46 (d, J=6 Hz, 1H), 7.74 (d, J=6 Hz, 1H), 8.20 (s, 1H), 8.57 (bs, 1H). High Resolution Mass Spectroscopy, calculated for C$_{23}$H$_{23}$N$_4$F$_3$S$_1$: 444.5226; found: 444.1593.

EXAMPLE 38

General Procedure for the Synthesis of 3-Glyoxamid [3-N-methylglyoxamid)-5)cyanoindole The procedure as described in Example 9 was used. Dimethylamine was replaced with either anhydrous ammonia or anhydrous methylamine.

38A. 3-Glyoxamid-5-cyanoindole

Oxalyl chloride (9.16 ml, 0.1 mol) was added to a solution of 5-cyanoindole (10 g, 70.4 mmol) and phthalimide (4.14 g, 28 mmol) in dry diethyl ether (200 ml). The reaction mixture was than saturated with anhydrous ammonia. The title compound was isolated as a tan solid (14.1 g, 94%). $^1$H NMR (DMSO) $\delta = 7.60$–7.74 (m, 2H), 8.14 (bs, 1H), 8.52 (s, 1H).

38B. 3-(N-Methylglyoxamid)-5-cyanoindole

Oxalyl chloride (2.5 ml, 28.6 mmol) was added to a solution of 5-cyanoindole (3 g, 21.1 mmol) and phthalimide (1.1 g, 7.48 mmol) in dry diethyl ether (70 ml). The reaction mixture was than saturated with anhydrous ammonia. The title compound was isolated as a white solid (4.4 g, 92%). $^1$H NMR (DMSO) $\delta = 2.67$ (d, J=4 Hz, 3H), 6.61–6.74 (m, 2H), 8.54 (s, 1H), 8.76 (bs, 1H), 8.90 (s, 1H).

EXAMPLE 39

General Procedure for the Synthesis of 3-Glyoxamid (N-methylglyoxamid)-5-(thiocarboxamido)indole The procedure as described in Example 10 was used.

39A. 3-Glyoxamid-5-(thiocarboxamido)indole

A stirred solution of the compound of Example 38A (5 g, 23.5 mmol) in ethyl acetate (120 ml) was mixed with diethyl dithiophosphate (3.93 ml, 23.5 mmol). The title compound was isolated as a beige solid (4.5 g, 77.5%). $^1$H NMR (DMSO) $\delta = 7.46$ (d, J=6 Hz, 1H), 7.69 (bs, 2H), 7.76 (d, J=6 Hz, 1H), 8.03 (bs, 1H), 8.72 (s, 1H), 8.81 (s, 1H), 9.66 (bs, 1H).

39B. 3-(N-Methylglyoxamid)-5-(thiocarboxamido)indole

A stirred solution of the compound of Example 38B (3 g 13.2 mmol) in ethyl acetate (60 ml) was combined with diethyldithiophosphate (2.2 ml, 13.2 mmol). The title compound was isolated as a yellow solid (3.3 g, 97% ). $^1$H NMR (DMSO) $\delta$=2.76 (d, J=2 Hz, 3H), 7.51 (d, J=8 Hz, 1H), 7.80 (d, J=8 Hz, 1H), 8.66 (d, J=4 Hz, 1H), 8.79 (d, J=4 Hz, 1H), 9.47 (bs, 1H), 9.69 (bs, 1H).

EXAMPLE 40

General Procedure for the Synthesis of 2{[3-Glyoxamid (3-N-methylglyoxamid)]indol-5-yl}-4-benzylthiazole Procedure identical as described in Example 11.

40A. 3-(3-Glyoxamidindol-5-yl-4-benzylthiazole

A mixture of the compound of Example 39A ( 0.34 g, 1.36 mmol) and 1-chloro-3-phenyl-2-propanone (0.23 g, 1.36 mmol) in isopropanol (25 ml) was refluxed for 4 hours. The title compound was isolated as a beige solid (0.41 g, 83.5%). $^1$H NMR (CDCl$_3$) $\delta$=4.18 (s, 2H), 6.67 (s, 1H), 7.18–7.32 (m, 6H), 7.40 (d, J=6 Hz, 1H), 7.94 (d, J=6 Hz, 1H), 8.88 (s, 1H), 8.94 (bs, 1H).

40B. 2-[3-(N-Methylglyoxamid)indol-5-yl]-4-benzylthiazole

A mixture of the compound of Example 39B (0.36 g, 1.36 mmol) and 1-chloro-3-phenyl-2-propanone (0.23 g, 1.36 mmol) in isopropanol (25 ml) was heated at reflux temperature for hours. The title compound was isolated as a beige solid (0.35 g, 69%). $^1$H NMR (DMSO) $\delta$=2.77 (s, 3H), 4.16 (s, 2H), 7.18–7.26 (m, 1H), 7.31 (s, 1H), 7.32–7.39 (m, 5H), 7.61 (d, J=6 Hz, 1H), 7.84 (d, J=6 Hz, 1H), 8.67–8.75 (m, 1H), 8.78 (s, 1H), 8.92 (bs, 1H).

EXAMPLE 41

General Procedure for the Synthesis is of 2-{[3-Amino (3-N-methylamino) ethyl]indol-5-yl}-4-benzylthiazole Procedure identical as described in Example 22 and 23.

41A. 2-[3-(Aminoethyl)indol-5-yl]-4-benzylthiazole

The compound of Example 40A (0.38 g, 1.05 mmol) was reduced with 1M borane in tetrahydrofuran (4 ml, 4 mmol) using identical procedure as described in Example 22. The crude product was isolated as a borane complex (0.3 g, 83%). Conversion of the borane complex by the procedure described in Example 23 afforded the title compound (0.11 g, 46%) as a colorless resin. $^1$H NMR (CDCl$_3$) $\delta$=2.92 (t, J=5 Hz, 2H), 3.03 (t, J=5 Hz, 2H), 4.21 (s, 2H), 6.64 (s, 1H), 7.02 (s, 1H), 7.27–7.33 (m, 6H), 7.75 (d, J=6 Hz, 1H), 8.16 (s, 1H), 8.52 (bs, 1H). High Resolution Mass Spectroscopy, calculated for C$_{20}$H$_{19}$N$_3$S$_1$: 333.4571; found 333.1281.

41B. 2-[3-(N-Methylaminoethyl)indol-5-yl]-4-benzylthiazole

The compound of Example 40B (0.28 g, 0.75 mmol) was reduced with 1M borane in tetrahydofuran (3 ml, 3 mmol) using identical procedure as described in Example 22. The crude product was isolated as a butane complex (0.22 g, 81%). Conversion of the borane complex by the procedure described in Example 23 afforded the title compound (85 mg, 44.5%) as a colorless resin. $^1$H (CDCl$_3$) $\delta$=2.42 (s, 3H), 2.84–2.98 (m, 4H), 4.20 (s, 2H), 6.62 (s, 1H), 6.69 (e, 1H), 7.25–7.33 (m, 6H) t 7.73 (d, J=6 Hz, 1H), 8.15 (s, 1H), 8.59 (bs, 1H). High Resolution Mass Spectroscopy, calculated for C$_{21}$H$_{21}$N$_3$S$_1$: 347.4839; found 347.1450.

I claim:

1. A compound of the formula

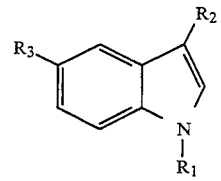

wherein R$_1$ is hydrogen, C$_1$ to C$_6$ alkyl, phenyl, benzyl, —COR$_4$, or —SO$_2$R$_4$; R$_2$ is

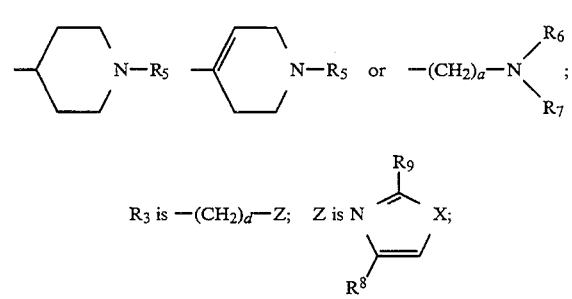

R$_3$ is —(CH$_2$)$_d$—Z;  Z is N

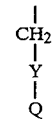

R$_4$ is C$_1$ to C$_6$ alkyl, phenyl, or benzyl; R$_5$ is hydrogen or C$_1$ to C$_6$ alkyl; R$_6$, R$_7$, R$_{11}$ R$_{12}$, and R$_{13}$ are each independently hydrogen or C$_1$ to C$_6$ alkyl; either one of R$_8$ or R$_9$ is hydrogen, C$_1$ to C$_6$ alkyl, halogen-substituted C$_1$ to C$_6$ alkyl, 1-pyrrolidynylmethyl, 1-piperidynylmethyl, cyclopentylmethyl, cyclohexylmethyl or

|
CH$_2$
|
Y
|
Q with the other of R$_8$ or R$_9$ being the bond between R$_3$ and Z; Q is

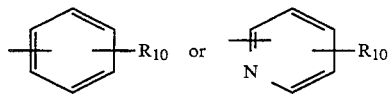

R$_{10}$ is hydrogen, hydroxy, halogen, cyano, nitro, —CF$_3$, —NR$_{11}$R$_{12}$, C$_1$ to C$_6$ alkyl, or —O—(CH$_2$-)$_b$—CH$_3$; X is S, O, or S→O; Y is a covalent bond, C$_1$ to C$_5$ alkyl, S, O, NR$_{13}$, *—(CH$_2$)$_c$—NR$_{13}$, —N—(CH$_2$-)$_c$—CH$_3$, *—(CH$_2$)$_c$—S—(CH$_2$)$_f$—, *—(CH$_2$-)$_c$—O—(CH$_2$)$_f$—, *—(CH$_2$)$_c$—(C=O)—NR$_{13}$, *—(CH$_2$)$_c$SO$_2$—NR$_{13}$, *—(CH$_2$)$_c$—NR$_{13}$—(C=O)—, or *—(CH$_2$)$_c$—NR$_{13}$—SO$_2$— wherein the * in the foregoing groups indicates the point of attachment to the methylene moiety; b, d, and f are each independently 0, 1, 2, or 3; a is 1, 2, or 3; and c is 0, 1 or 2, and a pharmaceutically acceptable salt thereof.

2. The compound according to claim 1, wherein R$_2$ is

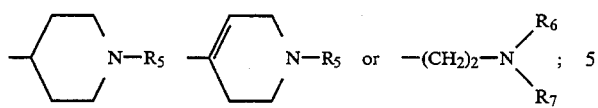

and R₆ and R₇ are each —CH₃.

3. The compound according to claim 2, wherein X is S; R₈ is

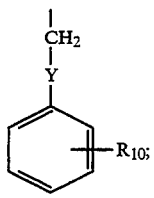

Y is a direct bond,

S, or O; and R₁₀ is H or —OCH₃.

4. The compound of claim 1, wherein X is S and R₂ is

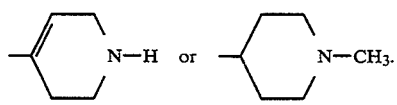

5. The compound of claim 4, wherein R₃ is

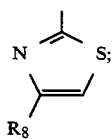

and R₈ is H, —CH₃, or

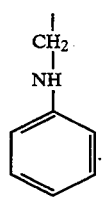

6. The compound of claim 4, wherein f is O and R₃ is

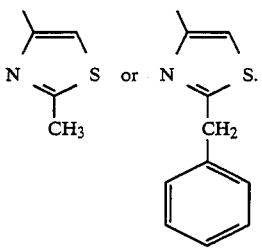

7. The compound of claim 1, wherein said compound is selected from the group consisting of:
2-[3-(N,N-dimethylaminoethyl)indol-5-yl]-4-(phenylaminomethyl)thiazole;
2-[3-(N,N-dimethylaminoethyl)indol-5-yl]-4-(benzylaminomethyl)thiazole;
2-[3-(N,N-dimethylaminoethyl)indol-5-yl]-4-(phenylthiomethyl)thiazole;
2-[3-(N,N-dimethylaminoethyl)indol-5-yl]-4-(phenoxymethyl)thiazole;
2-[3-(N,N-dimethylaminoethyl)indol-5-yl]-4-(2-methoxyphenylaminomethyl)thiazole;
2-[3-(N,N-dimethylaminoethyl)indol-5-yl]-4-(3-methoxyphenylaminomethyl)thiazole;
2-[3-(N,N-dimethylaminoethyl)indol-5-yl]-4-(4-methoxyphenylaminomethyl)thiazole;
2-[3-(1,2,5,6-tetrahydropyrid-4-yl)indol-5-yl]thiazole;
2-[3-(1,2,5,6-tetrahydropyrid-4-yl)indol-5-yl]-4-methylthiazole;
4-[3-(1,2,5,6-tetrahydropyrid-4-yl)indol-5-yl]-2-methylthiazole;
2-[3-(1,2,5,6-tetrahydropyrid-4-yl)indol-5-yl]-4-(phenylaminomethyl)thiazole;
2-[3-(1-methylpiperidin-4-yl)indol-5-yl]-4-(phenylaminomethyl)thiazole;
2-[3-(N,N-dimethylaminoethyl)indol-5-yl]-4-benzylthiazole;
2-[3-(N,N-dimethylaminoethyl)indol-5-yl]-4-phenethylthiazole;
2-[3-(Aminoethyl)indol-5-yl]-4-benzylthiazole;
2-[3-(N-Methylaminoethyl)indol-5-yl]-4-benzylthiazole; and
4-[3-(N,N-Dimethylaminoethyl)indol-5-yl]-2-benzylthiazole.

8. A pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound according to claim 1 effective in treating such condition and a pharmaceutically acceptable carrier.

9. A pharmaceutical composition for treating disorders arising from deficient serotonergic neurotransmission comprising an amount of a compound according to claim 1 effective in treating such a disorder and a pharmaceutically acceptable carrier.

10. A method for treating a condition selected from hypertension, depression, anxiety, eating disorders, obesity, drug abuse, cluster headache, migraine, pain and chronic paroxysmal hemicrania and headache associated with vascular disorders comprising administering to a mammal requiring such treatment an amount of a compound according to claim 1 effective in treating such condition.

11. A method for treating disorders arising from deficient serotonergic neurotransmission comprising administering to a mammal requiring such treatment an amount of a compound according to claim 1 effective in treating such a disorder.

12. A compound of the formula

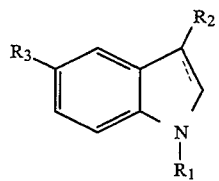

I wherein a broken line represents an optional double bond; $R_1$ is hydrogen, or a protecting group; $R_2$ is hydrogen or

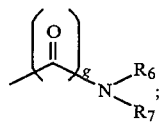

$R_3$ is —$(CH_2)_d$—Z; Z is

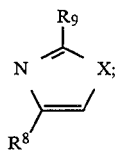

$R_5$ is hydrogen or $C_1$ to $C_6$ alkyl; $R_6$, $R_7$, $R_{11}$, $R_{12}$, and $R_{13}$ are each independently hydrogen or $C_1$ to $C_6$ alkyl; either $R_8$ or $R_9$ is hydrogen, $C_1$ to $C_6$ alkyl, halogen-substituted $C_1$ to $C_6$ alkyl, or

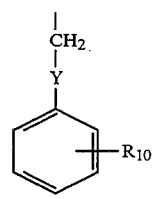

with the other being the bond between $R_3$ and Z, with the proviso that when $R_9$ is the bond between $R_3$ and Z, the broken line represents a double bond, and when $R_8$ is the bond between $R_3$ and Z and $R_1$ is a protecting group the broken line is not a double bond; $R_{10}$ is hydrogen, hydroxy, halogen, cyano, nitro, —$CF_3$, —$NR_{11}R_{12}$, $C_1$ to $C_6$ alkyl, or —O—$(CH_2)_b$—$CH_3$; X is S, O, or S→O; Y is a covalent bond, $C_1$ to $C_5$ alkyl, S, O,

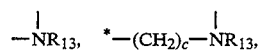

—N—$(CH_2)_c$—$CH_3$,  *—$(CH_2)_c$—S—$(CH_2)_f$—,
*—$(CH_2)_c$—O—$(CH_2)_f$—, *—$(CH_2)_c$—(C=O)—$NR_{13}$,

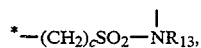

*—$(CH_2)_c$—$NR_{13}$—(C=O)—, or *—$(CH_2)_c$—$NR_{13}SO_2$— wherein the * in the foregoing indicates the point of attachment to the methylene moiety; b, d, and f are each independently 0, 1, 2, or 3; g are 1, 2, or 3; and c is 0, 1 or 2, with the proviso that when $R_1$ is a protecting group, $R_2$ is hydrogen, and the pharmaceutically acceptable salts thereof.

13. The compound of claim 12, wherein said protecting groups are phenyl sulfonyl, acetyl, tert-butoxycarbonyl, or para-toluenesulfonyl.

* * * * *